US009746378B2

(12) United States Patent
Rahman

(10) Patent No.: US 9,746,378 B2
(45) Date of Patent: *Aug. 29, 2017

(54) TERAHERTZ TIME DOMAIN AND FREQUENCY DOMAIN SPECTROSCOPY

(71) Applicant: Anis Rahman, Hummelstown, PA (US)

(72) Inventor: Anis Rahman, Hummelstown, PA (US)

(73) Assignee: Applied Research and Photonics, Inc., Harrisburg, PA (US)

(*) Notice: Subject to any disclaimer, the term of this patent is extended or adjusted under 35 U.S.C. 154(b) by 318 days.

This patent is subject to a terminal disclaimer.

(21) Appl. No.: 14/311,859

(22) Filed: Jun. 23, 2014

(65) Prior Publication Data

US 2014/0299771 A1    Oct. 9, 2014

Related U.S. Application Data

(63) Continuation of application No. 12/322,662, filed on Feb. 5, 2009, now Pat. No. 8,759,778, which is a continuation-in-part of application No. 11/862,474, filed on Sep. 27, 2007, now Pat. No. 8,050,531, and a continuation-in-part of application No. 11/862,473, filed on Sep. 27, 2007, now Pat. No. 7,919,755.

(60) Provisional application No. 61/026,233, filed on Feb. 5, 2008.

(51) Int. Cl.

| G01N 21/35 | (2014.01) |
| G01J 3/45 | (2006.01) |
| G01J 3/02 | (2006.01) |
| G01J 3/42 | (2006.01) |
| G01N 21/3586 | (2014.01) |
| G02F 1/35 | (2006.01) |
| G02F 1/355 | (2006.01) |
| G01J 3/26 | (2006.01) |
| G01N 21/90 | (2006.01) |

(52) U.S. Cl.
CPC . *G01J 3/45* (2013.01); *G01J 3/02* (2013.01); *G01J 3/0232* (2013.01); *G01J 3/26* (2013.01); *G01J 3/42* (2013.01); *G01N 21/3586* (2013.01); *G02F 1/353* (2013.01); *G02F 1/3558* (2013.01); *G01N 21/9027* (2013.01); *G02F 2203/13* (2013.01)

(58) Field of Classification Search
CPC .... G01N 21/55; G01N 21/9501; G01N 21/35; G01N 3/4833; G01N 3/45; G01N 3/26
USPC .... 250/341.1, 390.07, 338.3, 339.08, 339.02
See application file for complete search history.

(56) References Cited

U.S. PATENT DOCUMENTS

| 7,389,029 B2* | 6/2008 | Rahman | B82Y 30/00 385/129 |
| 7,391,032 B1* | 6/2008 | Hyde | G01J 1/4228 250/394 |
| 2003/0163042 A1* | 8/2003 | Salmon | G01S 13/04 600/436 |
| 2004/0022475 A1* | 2/2004 | Pennington | B82Y 20/00 385/12 |

(Continued)

*Primary Examiner* — David Porta
*Assistant Examiner* — Djura Malevic
(74) *Attorney, Agent, or Firm* — Volpe and Koenig, P.C.

(57) ABSTRACT

Terahertz spectrometer having a wider range of terahertz radiation source, high temporal resolution of scanning (<0.0.099 μm or ~0.3 pico second) over a wider range of scanning (up to ~100 pico seconds). Also disclosed are exemplary applications of the spectrometer in biomedical, biological, pharmaceutical, and security areas.

16 Claims, 23 Drawing Sheets

(56) References Cited

U.S. PATENT DOCUMENTS

2006/0268945 A1* 11/2006 Minamide .......... G01N 21/3581
  372/6
2007/0195921 A1* 8/2007 Ouchi .................... G01N 22/00
  378/1
2007/0263682 A1* 11/2007 Zhang ................ G01N 21/3581
  372/25
2008/0007817 A1* 1/2008 Hochberg ............... H01S 3/063
  359/333

* cited by examiner

TERAHERTZ TIME DOMAIN AND FREQUENCY DOMAIN SPECTROSCOPY

CROSS REFERENCE TO RELATED APPLICATIONS

The present application is a Continuation of U.S. Nonprovisional application Ser. No. 12/322,662 filed 5 Feb. 2009, which is a continuation-in-part of U.S. Pat. No. 7,919,755 filed Sep. 27, 2007 and U.S. Pat. No. 8,050,531, filed Sep. 27, 2007 which claim the benefit of U.S. Provisional Application Ser. No. 61/026,233 filed 5 Feb. 2008, all of which are herein incorporated in their entireties.

BACKGROUND OF THE INVENTION

The present invention relates to terahertz time domain and frequency domain spectroscopy using dendrimer based terahertz sources.

The recently accessible terahertz (THz) portion of the electromagnetic spectra, also known as T-ray spectra, has a wide potential to be employed in important fundamental research, medical, biomedical, and biological studies. When converted to other units, 1 THz is equivalent to 33.33 cm$^{-1}$ (wave numbers), 0.004 eV photon energy, or 300 µm wavelength. THz spectroscopy covers the region of electromagnetic spectrum from 0.3 THz to ~20 THz (from 10 to 600 cm$^{-1}$), with most of the work being done between 0.5 and ~3 THz range.

While Fourier-transform infrared (FT-IR) spectroscopy can monitor alterations at individual bonds even in some protein complexes, thus allow monitoring structural and conformational changes in the course of a biological reaction, yet, presently available frequency range of FT-IR techniques, typically 4000-400 cm$^{-1}$ (~120-12 THz) does by far not cover the full range of functionally relevant modes of enzymes and proteins, which may extend down to 10 cm$^{-1}$ (0.3 THz). This can only be done with THz spectroscopy.

To understand the interaction of far-infrared (FIR) and THz radiation with biological systems on a molecular level, i.e. on the basis of resonant processes with electronic, vibrational, and rotational states of complex biological molecules in relation to a modulation of their biological activity, which can be stimulation, inhibition, and in the worst case damage, the functionally relevant states are probed by near- and mid-infrared spectroscopy (6000 cm$^{-1}$–500 cm$^{-1}$), e.g., absorbance and reaction-induced difference spectra of structurally and functionally intact biological samples of proteins and enzymes. However, because many important biological events, as mentioned above, occur in the THz range, information obtained via FT-IR is not complete or sometimes insufficient. Thus, THz spectroscopy is an important tool to aid in the understanding of many crucial biological activities. Also, THz spectroscopy can uniquely discern between molecular polymorphs, hybridized and denatured DNAs, and other bio-molecular complexes of interest that can not be done with other methods such as FT-IR.

Techniques such as X-ray crystallography, 2-D NMR spectroscopy, and high-resolution electron microscopy deliver static, frozen-in-time pictures of proteins, enzymes, and biological membranes as opposed to real time live image obtainable by T-rays.

Information on the function and how it is related to the structure, requires spectroscopic techniques which probe structural properties and allow high temporal resolution on the order of pico seconds. This can not be obtained by anything other than T-ray spectroscopy.

Among the variety of spectroscopic techniques, Infrared (IR) spectroscopy has probably the best access to minute structural details, in the order of fractions of a bond dimension. Infrared spectroscopy has greatly advanced sensitivity and rapid data acquisition capabilities provided by Fourier-Transform infrared (FT-IR) spectrometers. This is still not comparable with the capabilities of T-ray spectra, because of the lack of high resolution temporal information.

These existing and promising THz applications have brought upon challenges for spectroscopy techniques as well as THz emitters and sensors. For spectroscopic applications, efficient and broadband THz radiation is necessary. Also sensitive and broad frequency response THz sensors are critical for some spectroscopy techniques.

THz emission by the electro-optic rectification (EOR) effect of electro-optic (EO) materials and THz detection by EO sampling is one method for obtaining ultra-broadband THz field. The key parts of this all-optical high resolution THz spectroscopy are to deploy high EO efficiency materials for terahertz generation and an ultra-short laser pulse source to activate the EOR effect. A second approach is to use difference frequency generation (DFG), where, a pair of lasers can be used to excite the rectification effect in an EO material. This is also known as difference frequency mixing (DFM), because, here the generated terahertz radiation wavelength falls in the region which is equal to the difference of the two pump lasers. The lasers can be pulsed to produce a pulsed THz output or CW that produces CW T-rays.

DETAILS DESCRIPTION OF PREFERRED EMBODIMENT

Overview and Theory

Figure 1:
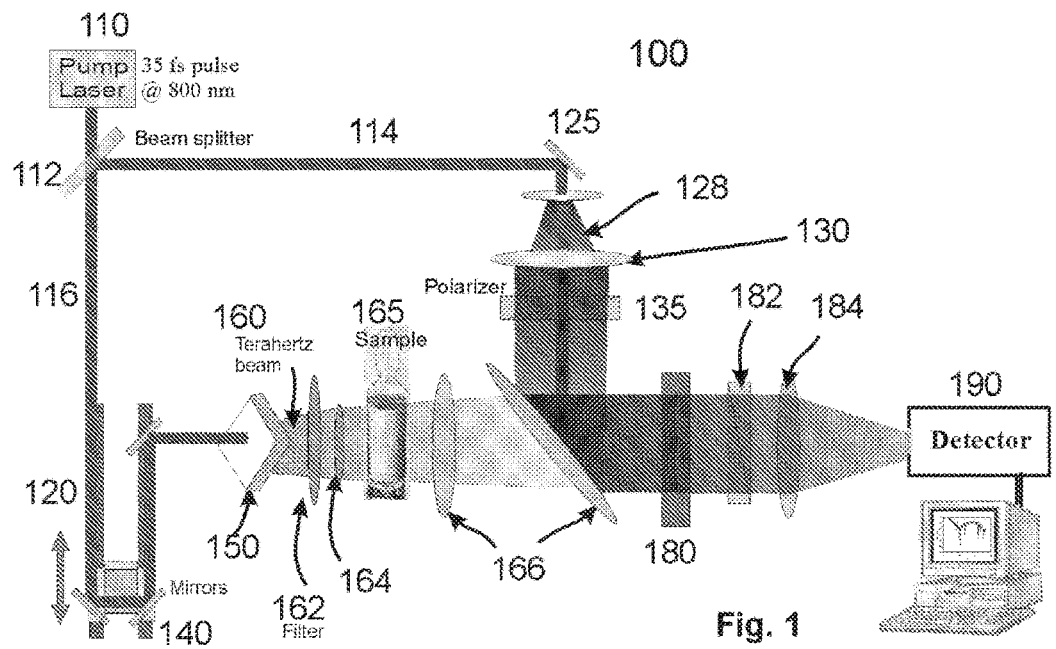
FIG. 1 shows an exemplary embodiment of a terahertz spectrometer.

Electro-optic properties are important for many photonic devices that generally exploit the non linear optical parameters such as the second order susceptibility, $\chi^{(2)}$. These devices include terahertz emitter, optical modulator, and electro-optic sensors, among others. Dendrimers are a class of star burst polymers with nearly spherical, mono-dispersed molecular architecture. Unlike side chain polymers, dendrimer structure is characterized by three distinct features: (i) a central multifunctional core, (ii) nearly spherical shells or "generations" of multifunctional repeat units attached around the core, and (iii) surface or end groups that are also multifunctional. Manipulating these structural features allows a controlled enhancement of optical and electro-optic properties of these end-functionalized macromolecules. For instance, when chemically complexed (doped) with a dopant such as a chromophore, dendrimer's nonlinear optical properties can be enhanced significantly.

A high $\chi^{(2)}$ dendrimer for terahertz generation is used in the present invention. A terahertz time-domain spectroscopy (THz-TDS) is described where a dendrimer source and a dendrimer sensor is used for electro-optic sampling type detection. The temporal behavior is examined and a Fourier analysis is conducted to investigate the frequency domain behavior. Additionally, measurements of single-stranded and double-stranded 25-mer oligonucleotides have been conducted that shows an effective means of distinguishing between these two DNAs by THZ-TDS. The measurements also allow for discerning between different concentrations (dose) of DNA specimens of the same group with biologically available quantities.

Terahertz radiation from dendrimer can be generated either (i) by electro-optic rectification (EOR) or (ii) by difference frequency mixing (DFM). An advantage of using the electro-optic route (EOR or DFM) is the inherent power scalability of the approach, since it is not limited either by THz emission saturation or by heat dissipation. Also, the waveguide structure allows raising the effective pump intensity significantly. As an amorphous electro-optic medium, dendrimer removes the directional dependence of power generation and angular dependence of pump intensity that is imposed by the Reststrahlen bands in crystalline media. Pumping a number of waveguide in an array by a single pump plays an important role in increasing the efficiency. The combined effect of these factors in electro-optic dendrimer allows generating higher average terahertz power at room temperature.

The fact that THz pulses generated by electro-optic rectification are created and detected using short-pulsed lasers with pulse widths ranging from ~100 fs down to ~10 fs adds a new element that is not present in conventional far-IR studies—it is possible to carry out time-resolved far-IR studies with pico or sub-picosecond temporal resolution. In contrast, other sources of far-IR radiation such as arc lamps or globars are continuous, and pulsed sources such as free electron lasers or synchrotrons typically produce far-IR pulses with ~3 ps duration or greater.

Another mechanism is the so called difference frequency mixing (DFM) or difference frequency generation (DFG). The DFG method is also an electro-optic route but here two pump lasers of two different wavelengths are mixed within the EO dendrimer to create what is known as the difference frequency. Terahertz frequency generated by DFG method is tunable, because it is proportional to the difference of two optical frequencies used to excite the polarizations: $f_{THz} \alpha v_2 - v_1$, where, $v_1$ and $v_2$ are the frequencies of laser-1 and laser-2, respectively. $f_{THz}$ is much smaller than both $v_1$ and $v_2$; and in principle, can be tuned by choosing appropriate pump lasers. However, in practice, it is not obvious to generate difference frequency in a given electro-optic medium. More research is necessary to work out a scheme that involves understanding the physics, chemistry and engineering of this technique. Despite these difficulties, DFG has been used to generate terahertz radiation in silicon waveguide with polymer cladding as shown in T. Baehr-Jones, M. Hochberg, Richard Soref, and A. Scherer, "Design of a tunable, room temperature, continuous-wave terahertz source and detector using silicon waveguides," J. Opt. Soc. Am. B/Vol. 25, No. 2/February 2008, p 261-268; in ZnTe as shown in Mark Cronin-Golomb, "Cascaded nonlinear difference-frequency generation of enhanced terahertz wave production," OPTICS LETTERS/Vol. 29, No. 17/Sep. 1, 2004, p 2046-2048; in AgGaS2 as shown in U. Simon, C. E. Miller, C. C. Bradley, R. G. Hulet, R. F. Curl, and F. K. Tittel, "Difference-frequency generation in AgGaS2 by use of single-mode diode-laser pump sources," OPTICS LETTERS/Vol. 18, No. 13/Jul. 1, 1993, p 1062-1064; and in poled LiNbO3 as shown in D. Richter, D. G. Lancaster, R. F. Curl, and F. K. Tittel, "Tunable, fiber coupled spectrometer based on difference-frequency generation in periodically poled lithium niobate," in Advanced Solid State Lasers, M. Fejer, H. Injeyan, and U. Keller, eds., Vol. 26 of OSA Trends in Optics and Photonics (Optical Society of America, 1999), paper WC5; and in DAST polymer as shown in K. Kawase, M. Mizuno, S. Sohma, H. Takahashi, T. Taniuchi, Y. Urata, S. Wada, H. Tashiro, and H. Ito, "Difference-frequency terahertz-wave generation from 4-dimethylamino-N-methyl-4-stilbazolium-tosylate by use of an electronically tuned Ti:sapphire laser," OPTICS LETTERS, Vol. 24, No. 15, 1999, p 1065-1067; and in GeSe as shown in W. Shi, M. Leigh, J. Zong, and S. Jiang, "Single-frequency terahertz source pumped by Q-switched fiber lasers based on difference-frequency generation in GaSe crystal," OPTICS LETTERS, Vol. 32, No. 8, 2007, p 949-951; and applicant has also demonstrated difference frequency generation from its proprietary EO dendrimer material as shown in A. Rahman "Dendrimer waveguide based high-efficiency terahertz source," Terahertz Technology and Applications, edited by Kurt J. Linden, Laurence P. Sadwick, Proc. of SPIE Vol. 6893, (2008), p 689302-1-689302-11.

An important advantage of THz spectroscopy is that the transient electric field itself is measured, not simply its intensity, and this determines the amplitude and phase of each of the spectral components that make up the pulse. The amplitude and phase are directly related to the absorption coefficient and index of refraction of the sample, and thus, the complex-valued permittivity of the sample can be obtained without having to carry out a Kramers-Kronig analysis. While methods exist for determining the index of refraction when using conventional far-IR sources and detectors, it is notable that the great majority of the far-IR results reported in the literature present the frequency-dependent absorption coefficient, but not the refractive index. In this respect, THz spectroscopy provides a convenient method for determining the complex permittivity, even for studies that are not time-resolved. The advantages of THz spectroscopy are: (1) It is a tabletop experiment with brightness equal to or exceeding that of synchrotron sources (at long wavelengths). (2) Coherent detection allows pulses below the blackbody radiation level to be measured without the use of specialized detectors. (3) Time-resolved studies are possible in the far-IR region of the spectrum.

An important factor in all terahertz spectroscopy is the available THz range. There are several factors that can affect the bandwidth of the generated and detected THz radiation. The first factor is the pump laser's bandwidth that interacts with the EO materials that generate the T-rays. For example, commercially available femto-second lasers can provide ~30 nm FWHM bandwidth centered at 800 nm. Corresponding FWHM bandwidth in the frequency domain is governed by the relationship, $$|\Delta f| = \frac{c|\Delta\lambda|}{\lambda_0^2} \quad (1)$$

where, $|\Delta f|$ is the terahertz frequency range, $|\Delta\lambda|$ is the FWHM of the femto-second pump laser, $\lambda_0$ is the center frequency of the femto laser, and c is the speed of light. This yields a range of ~14 THz. If all frequency components of the laser pulse and the corresponding THz radiation via the electro-optic rectification (EOR) process are perfectly phase matched inside the EO material, then the best FWHM bandwidth of the THz emission will be limited to ~14 THz. Other factors that limit the obtainable range are the dispersion of the nonlinear coefficients of the materials. This dispersion is strong around the Reststrahlen band of EO crystals. Another factor is dispersion of the complex refractive index n(.omega.), which is also closely related to the Reststrahlen band in the case of EO crystals. The dispersion of the real part of n(ω) results in a frequency dependent coherence length, or, velocity mismatch and the dispersion of the imaginary part of n(ω) results in the strong absorption around the Reststrahlen band. In order to experimentally achieve an ultra-broadband THz signal, it is also important that the optical probing pulse width be narrow enough to effectively sample the broadband THz radiation associated with the ultra-short electric field oscillation period.

An advantage of amorphous EO dendrimer of the current invention as THz emitter and sensor is that there is no Reststrahlen band, so that the dispersion effect does not limit the THz bandwidth as bad as in EO crystals where lattice resonance effect causes strong dispersion and absorption. Consequently, the obtainable terahertz range is limited primarily by the bandwidth of the femto-second pulsed pump laser.

Implementation and Materials

The electro-optic dendrimer terahertz source used in the embodiments below is discussed in U.S. patent application Ser. No. 11/862,473, filed Sep. 27, 2007, which was published as U.S. 20080128618 on Jun. 5, 2008 and U.S. patent application Ser. No. 11/862,474, filed Sep. 27, 2007, which was published as U.S. Publication No. 20080099698 on May 1, 2008, all of which are herein incorporated in their entireties. Briefly, the dendrimer is doped with a chromophore and poled at an elevated temperature at a high electric field. This process yields an electro-optic dendrimer with higher second order susceptibility, $\chi^{(2)}$, that is an uniaxial polar material because of the poling induced permanently broken centrosymmetry. The film is peeled off of the substrate to form a stand alone film after poling. The dipolar orientation is frozen-in by cooling the film while a high electric field is still being applied. A $r_{33}$ value of 120 pm/V is obtained at 800 nm leading to a higher $\chi^{(2)}$, according to the formula, $$\chi^{(2)} \alpha \epsilon^2 r_{33} \quad (2)$$

where, $r_{33}$ is the electro-optic coefficient, and .epsilon..sub.r is the relative permittivity given approximately by the square of refractive index. The measured refractive index of the film is ~1.52, hence $\chi^{(2)}$~277 pm/V at 800 nm. However, by controlling the doping, poling, and film forming parameters, the $\chi^{(2)}$ value can be varied over a wider range, e.g., 50 pm/V to 1000 pm/V.

Referring now to FIG. 1, there is shown a terahertz spectrometer 100. Terahertz spectrometer 100 includes a pump laser 110 such as for example, an 800 nm center wavelength femto-second pump laser. The beam from laser 110 is split in to two parts by a beam splitter 112 to establish a pump beam leg 116 and a probe beam leg 114. The two optical paths are carefully designed such that both the pump beam leg 116 and probe beam leg 114 face the same length of dispersive media. This serves as a group velocity dispersion (GVD) compensation mechanism, thus achieving the shortest pulse duration for both legs by adjusting the pulse compression mirrors of the femto-laser 110.

Figure 13:
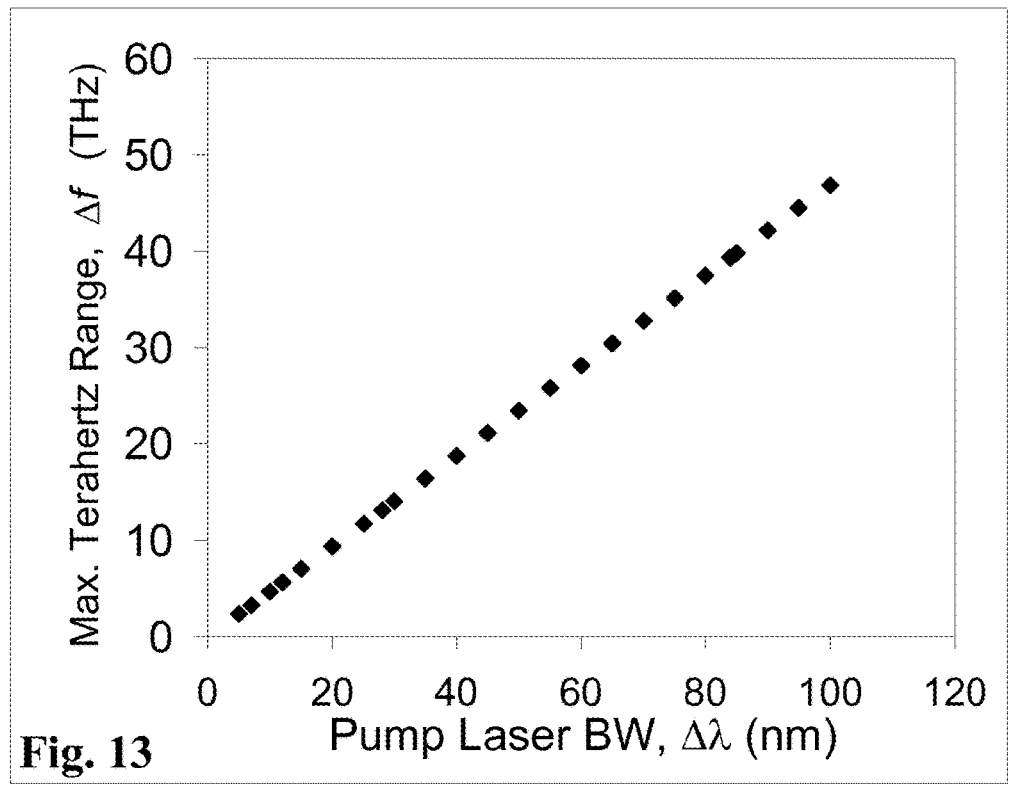
FIG. 13 shows a plot of terahertz range as a function of the pump laser's bandwidth.
Figure 14:
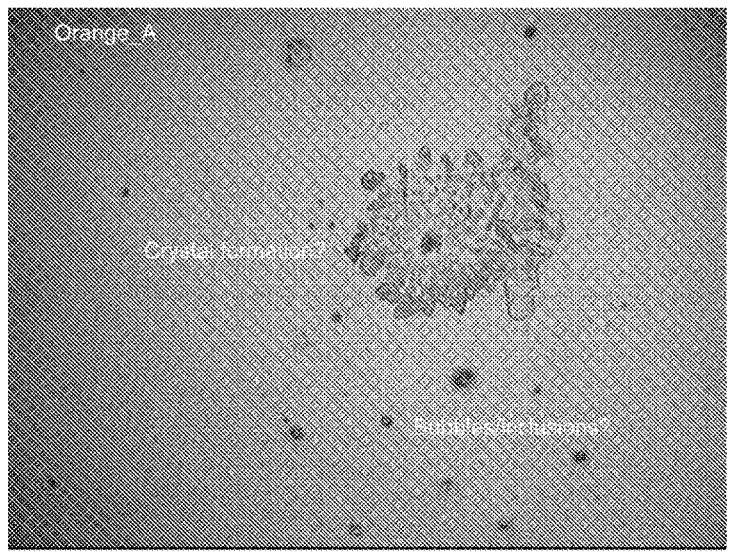
FIGS. 14*a-d* exhibits optical micrographs of DNA samples.
Figure 14:
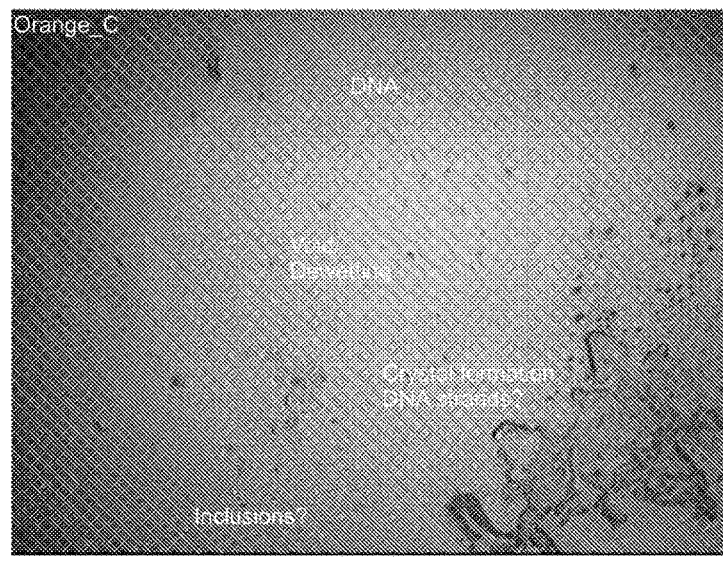
Figure 14:
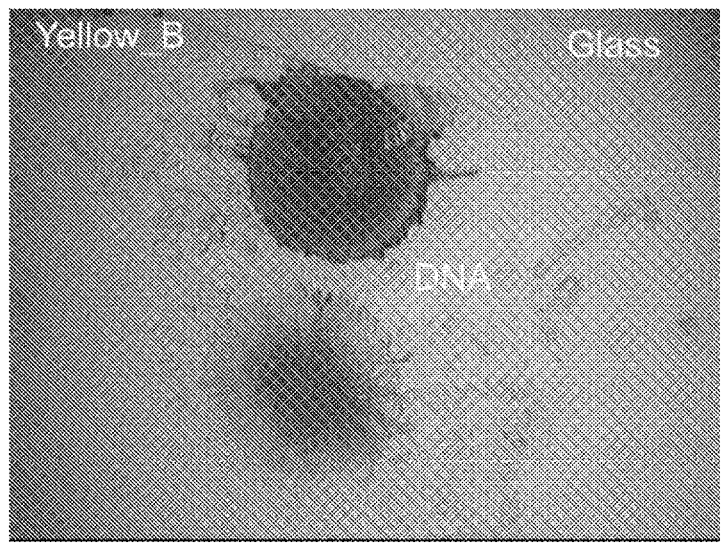
Figure 14:
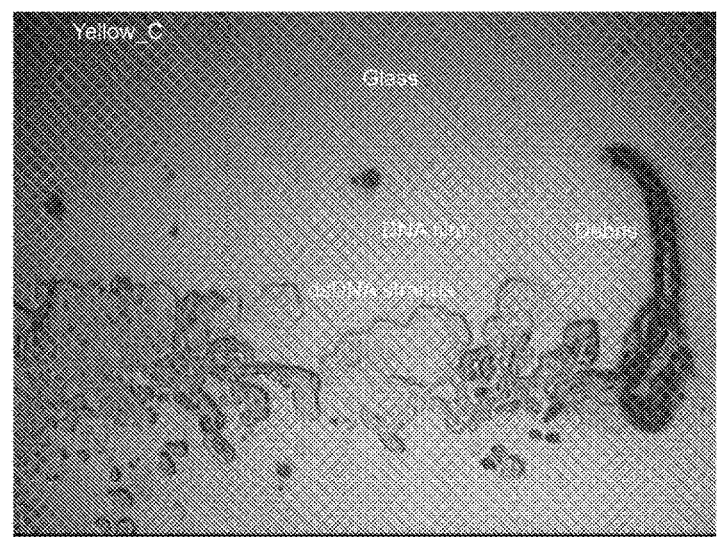

FIG. 13 shows a plot of terahertz range as a function of the femto-second pump laser's bandwidth according to Eq. (1). Thus, using a sub-15-fs pump laser that provides >60 nm emission bandwidth (or FWHM), the achievable THz radiation bandwidth can be broadened significantly. However, with such short laser pulse duration, both the second order and third order GVD have to be taken into consideration to obtain the shortest laser pulse-width. Unlike the second order GVD, the third order GVD can only be reduced by making the pulses pass through as short as possible dispersive media. This can be achieved by the free-standing films disclosed herein. For the same reason, the dendrimer films allow controlling the pulse broadening effect, yet it facilitates high intensity THz emission and sensitive THz detection.

The pump beam leg 116 further includes a computer controlled delay stage 120. The pump beam coming out of the delay stage 120 is then reflected off mirrors 140 and focused on terahertz emitter 150, which is for example, a dendrimer film as processed above. Terahertz emitter 150 produces a terahertz beam 160 which is directed through a sample 165 via a filter 162 and lens 164. The filter 162 filters out any residual beam coming from the pump beam and the lens 164 helps focusing of the beam on to the specimen. In order to achieve maximum THz emission, the angular orientation of the emitter film is adjusted such that the pump beam is incident at the Brewster's angle. Since the probe beam pulse-width should also be as short as possible, an identical glass slide may be inserted in the probe beam leg 114 (not shown). In the embodiment of FIG. 1, however, instead of a glass slide, a polarizer 135 and an analyzer 182 is used to perform equivalent functionality. In this way, both the pump and probe pulses are compressed to their shortest pulse duration.

In particular, this is critical because when light moves between two media of differing refractive index, generally some of it is reflected at the boundary. At one particular angle of incidence, however, light with one particular polarization cannot be reflected. This angle of incidence is the Brewster's angle, $\Theta_B$. The polarization that cannot be reflected at this angle is the polarization for which the electric field of the light waves lies in the same plane as the incident ray and the surface normal (i.e. the plane of incidence). Light with this polarization is called p-polarized, because it is parallel to the plane. Light with the perpendicular polarization is said to be s-polarized. When unpolarized light strikes a surface at Brewster's angle, the reflected light is always s-polarized.

The physical mechanism for this can be qualitatively understood from the manner in which electric dipoles in the media respond to p-polarized light. One can imagine that light incident on the surface is absorbed, and then reradiated by oscillating electric dipoles at the interface between the two media. The polarization of freely propagating light is always perpendicular to the direction in which the light is travelling. The dipoles that produce the transmitted (refracted) light oscillate in the polarization direction of that light. These same oscillating dipoles also generate the reflected light. However, dipoles do not radiate any energy in the direction along which they oscillate. Consequently, if the direction of the refracted light is perpendicular to the direction in which the light is predicted to be specularly reflected, the dipoles will not create any reflected light. Since, by definition, the s-polarization is parallel to the interface, the corresponding oscillating dipoles will always be able to radiate in the specular-reflection direction. This is why there is no Brewster's angle for s-polarized light. The radiated light transmitted from the film, in this case, is the terahertz radiation.

The probe beam leg 114 is used as a probing beam that is reflected by a mirror 125 onto an expander 127 and lens 130. The expander and lens combination works as a collimator such that the probing beam covers a wider area on the lens system 166. The probing beam then goes through a polarizer 135 and onto the lens system 166, which focuses the probing beam onto a probing sensor 180. Probing sensor 180 is a probing sensor made from high electro-optic efficiency dendrimer and serves as an image interrogator of the sample 165. The probing sensor 180 is necessary for probing the image carrying terahertz beam and is discussed in U.S. patent application Ser. No. 11/862,473, filed Sep. 27, 2007, and entitled "Dendrimer Based Electro-optic Sensor", which was published as U.S. 20080128618 on Jun. 5, 2008, and is incorporated herein by reference in its entirety. A polarizer 182 is placed in the probing beam leg 114 between the probing sensor 180 and detector 190 such that the detector 190 sees the same polarization of both probing and pump beams. A collimator 184 focuses the probing beam onto the detector 190.

Image interrogation by electro-optic probing utilizes terahertz induced birefringence of the probing sensor which results in a change of its polarization. A polarizer 135 and an analyzer 182 are placed perpendicular to each other in the beam path. The analyzer 182 is placed between the probing sensor and the CCD; thus the CCD sees the same polarization as the image. Phenomenologically, the probing beam can be thought of as a 'carrier' while the THz beam is the actual 'signal'.

Figure 2:
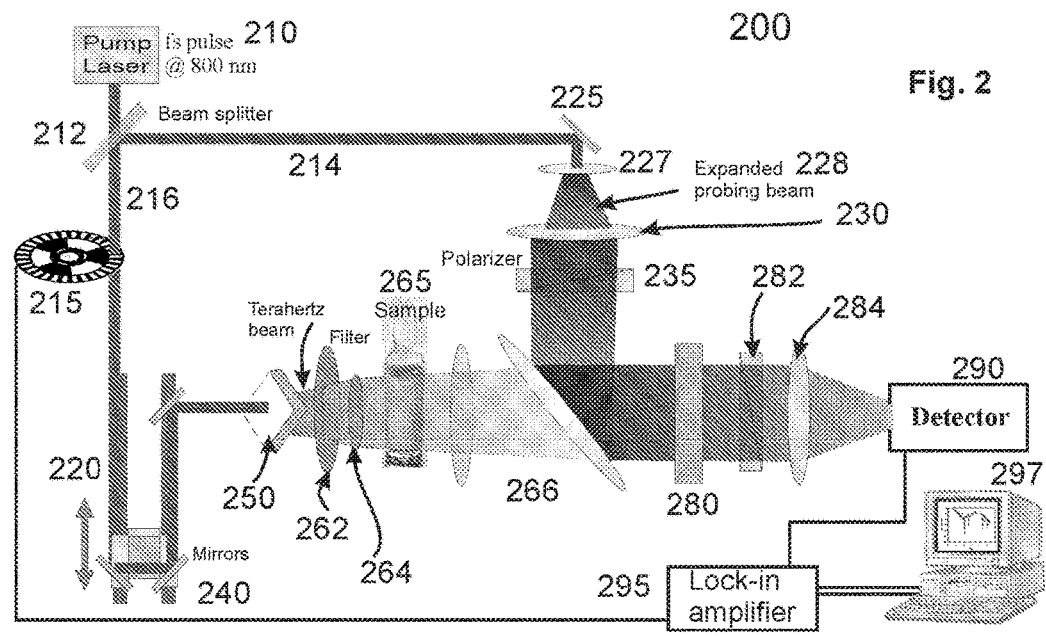
FIG. 2 shows an exemplary embodiment of a terahertz spectrometer with a chopper and lock-in amplifier circuit.

FIG. 2 shows an alternative configuration for a terahertz spectrometer 200 where the pump beam is modulated by a mechanical optical chopper 215 whose reference frequency is detected by a lock-in amplifier 295. The lock-in amplifier 295 reads in the detector 290 responses at the reference frequency. The lock-in amplifier 295 is controlled by a computer 297 to read the transient (or temporal) pulse. This arrangement is particularly important for pyroelectric detectors. Since low-cost pyroelectric detectors can sense in to far infrared regions, they are desirable under certain circumstances. However, because of the physical characteristics of pyroelectric detection, a low-frequency pulsed input is necessary; this is provided by the chopper.

Figure 3:
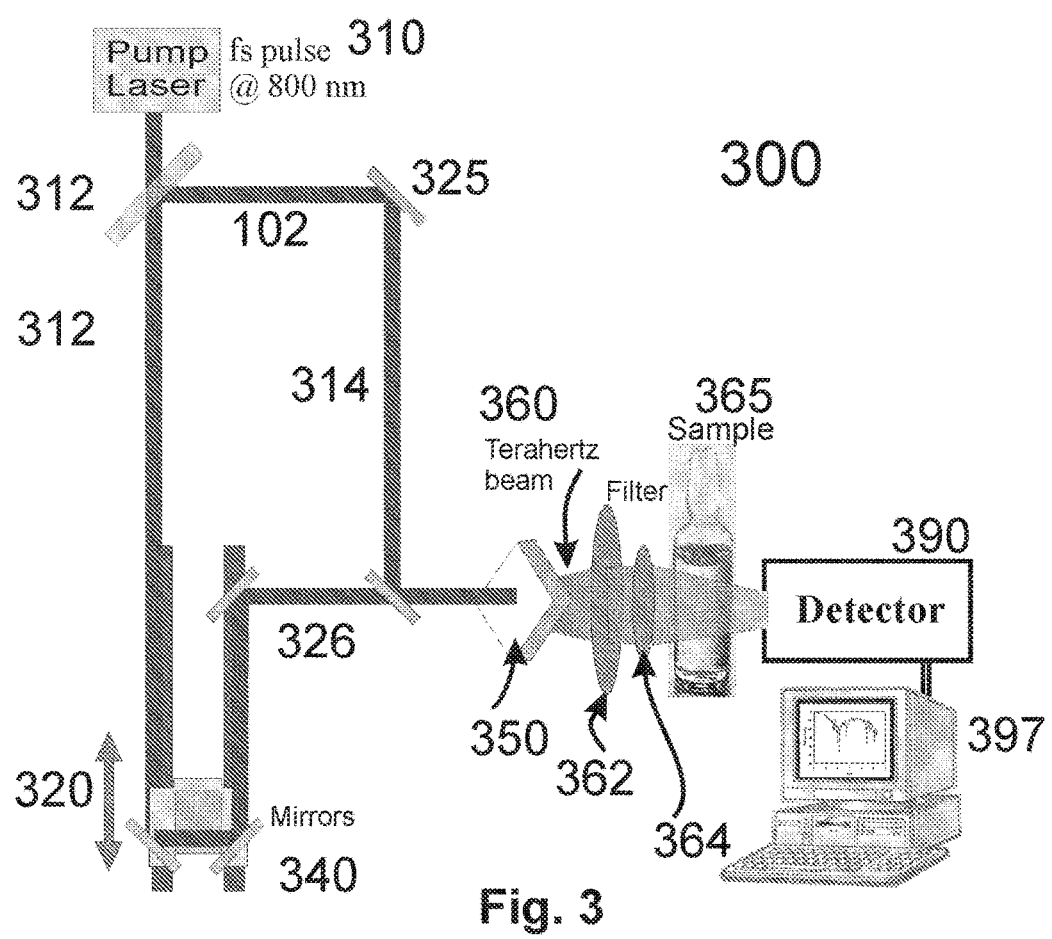
FIG. 3 shows an exemplary embodiment of a terahertz pulse measurement system.

FIG. 3 shows a setup for terahertz pulse measurement system 300. System 300 includes a pump laser 310 such as for example, an 800 nm center wavelength femto-second pump laser and a beam splitter 312 to establish a pump beam leg 316 and a probe beam leg 314. The pump beam leg 316 further includes a computer controlled delay stage 320. The pump beam coming out of the delay stage 320 is then reflected off mirrors 340 and 326 and focused on terahertz emitter 350, which is for example, a dendrimer film as processed above. Terahertz emitter 350 produces a terahertz beam 360, which is directed through a sample 365 via a filter 362 and lens 364. The probe beam leg 314 is used as a probing beam that is reflected by mirrors 325 and 326 and focused on terahertz emitter 350. The pump beam 316 and the probe beam 314 overlap directly on a THz emitter 350, forming an interference pattern at the right path difference created by the delay stage 320. The detector 390 is a high sensitivity thermopile type power meter. Here the formation of the temporal signal is formed via the interference of two coherent beams from the pump leg and probe leg, respectively. The probe leg 314 incident on the dendrimer emitter 350 remains stationary while the pump beam 316 scans the stationary beam on the emitter 350 as the delay stage travel over a predetermined distance. Consequently, consecutive constructive and destructive interference fringes form on the dendrimer emitter that causes a pulsed terahertz radiation to propagate onward through the sample on to the detector. The detector thus produces a pulse corresponding to a constructive interference pulse.

Figure 4:
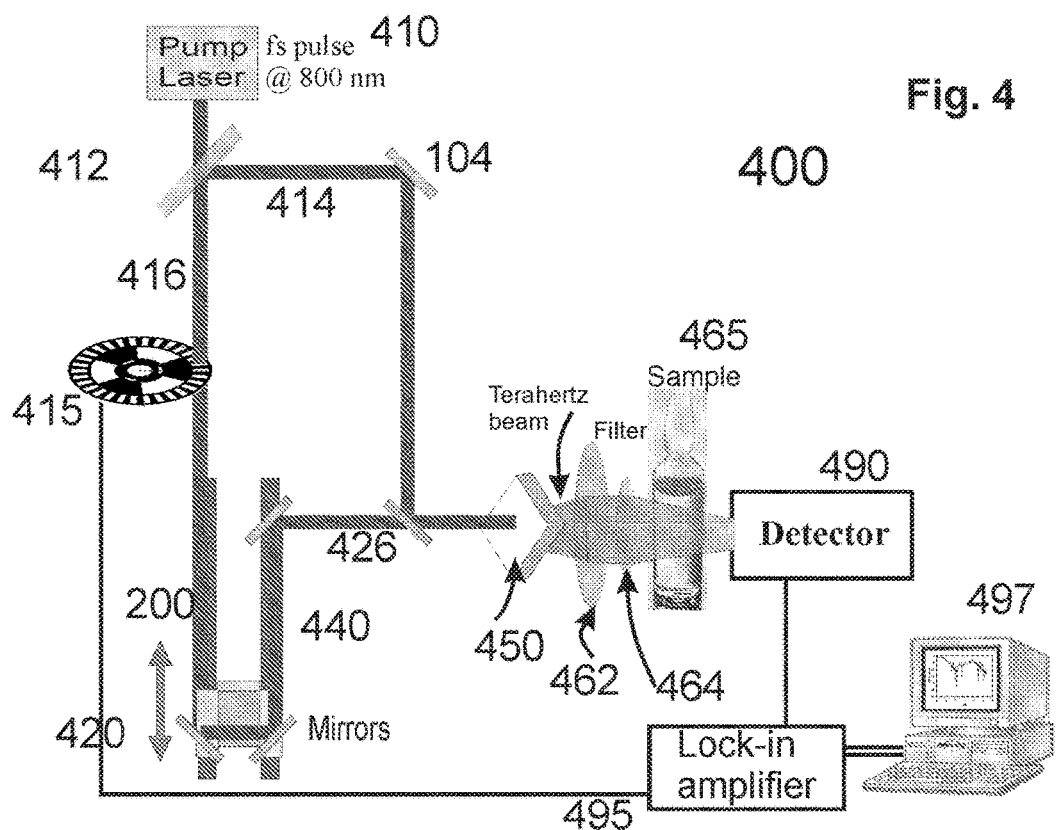
FIG. 4 shows an exemplary embodiment of a terahertz pulse measurement system with a chopper and lock-in circuit.

FIG. 4 shows an alternative setup for THz field measurement system 400 via a pyroelectric detector 490. Here a pump beam leg 416 includes a chopper 415 which modulates the pump beam and whose reference frequency is detected by a lock-in amplifier 495. The lock-in amplifier 495 reads in the detector 490 responses at the reference frequency. The lock-in amplifier 495 is controlled by a computer 497 to read the transient (or temporal) pulse. As before, this arrangement is important for pyroelectric detectors. Because of the physical characteristics of pyroelectric detection mechanism, a low-frequency pulsed input is necessary; this is provided by the chopper 415.

Figure 5:
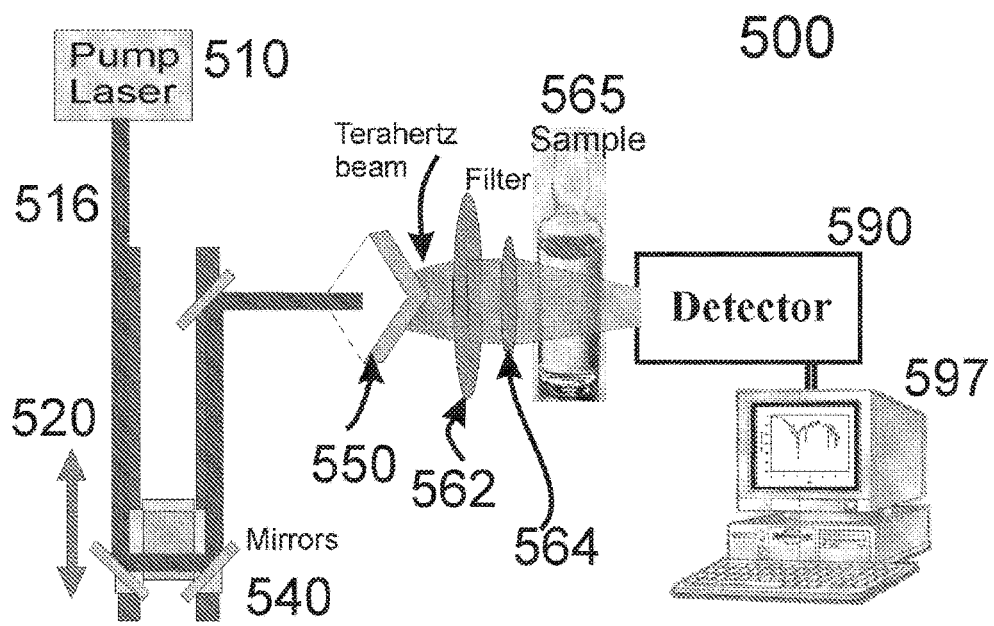
FIG. 5. shows an exemplary embodiment of a terahertz pulse measurement system in a self-interference arrangement.
Figure 6:
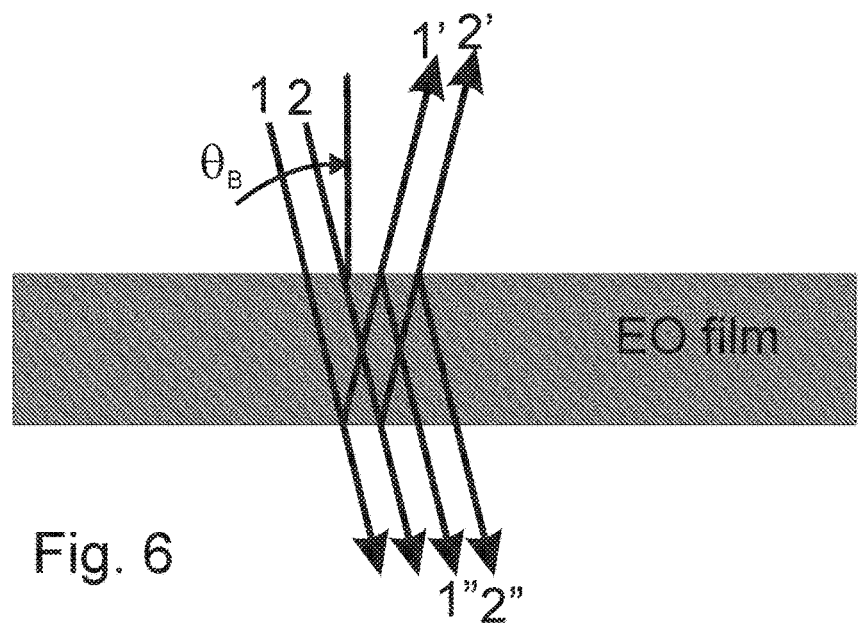
FIG. 6 illustrates the self-interference effect.

FIG. 5 shows a setup to measure the THz pulse measurement system 500 using a self-interference method. System 500 includes an 800 nm center wavelength femto-second pump laser 510. The pump beam 512 coming from the delay stage 520 is directly focused on to the dendrimer terahertz emitter 550. This beam forms a self-interference pattern via the mechanism shown in FIG. 6. That is, pump beam 516 or the incident beam is reflected back and forth from both surfaces of the emitter film that comprises the terahertz emitter 550. However, a reasonable dendrimer film thickness is necessary to be able to measure the self-interference fringes, because, if the film thickness is too small, it may not yield enough path difference for forming self-interference fringes. The detector 580 measures the intensity of the interference giving usually a single peak corresponding to the zero$^{th}$ order maxima. A chopper can be added along with a lock-in amplifier for pyroelectric detection.

Figure 7:
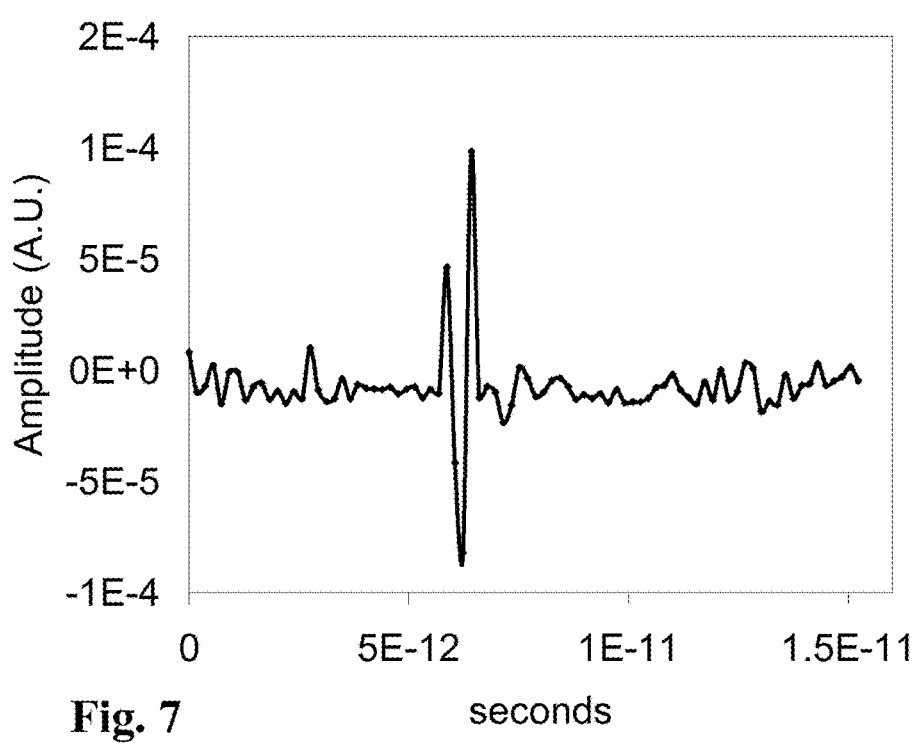
FIG. 7 shows an exemplary time domain terahertz pulse as read by a lock-in amplifier in the exemplary embodiments of FIGS. 2 and 4.

FIG. 7 shows a typical time-domain terahertz pulse as read through the lock-in amplifier 295 or 495 of FIG. 2 or FIG. 4, respectively. The pulse occurs over a very short time interval ranging from sub-picoseconds to a few picoseconds.

Figure 8:
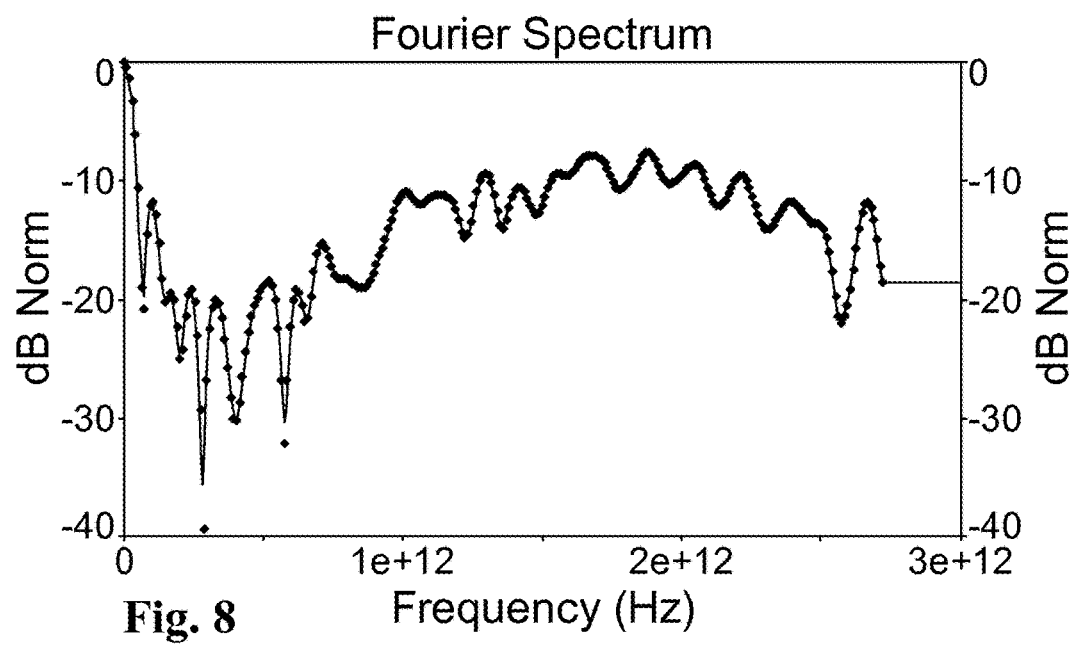
FIG. 8 shows the Fourier spectrum of the pulse shown in FIG. 7.

FIG. 8 shows the Fourier spectrum of the pulse of FIG. 7. This frequency domain spectrum spans up to 2.75 terahertz. This range can be further increased via suitable emitter and detector configurations along with the proper delay stage operation.

Figure 9:
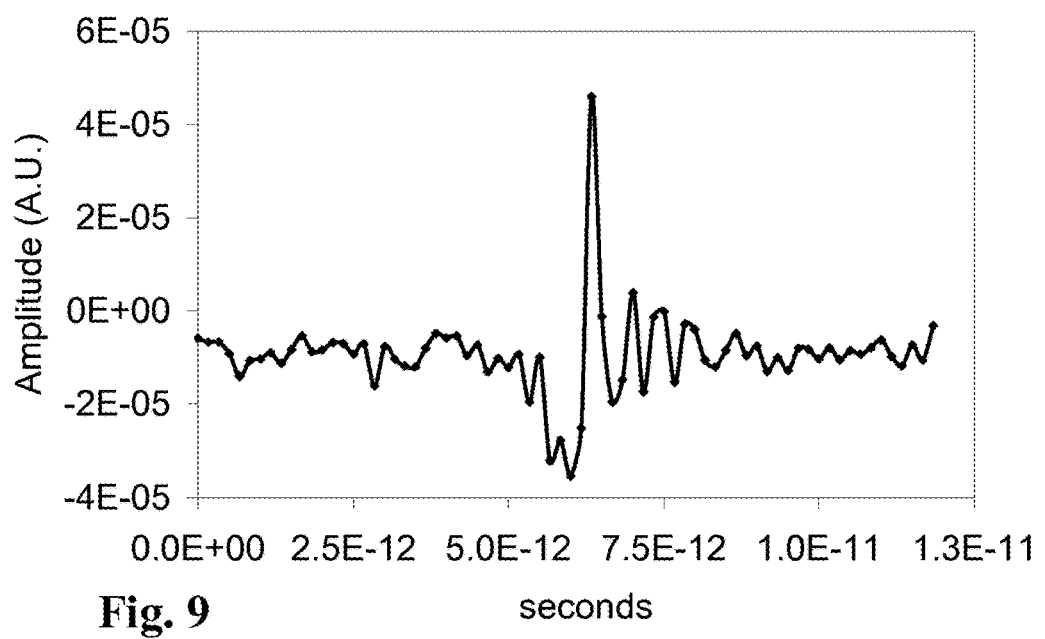
FIG. 9 shows an exemplary time domain terahertz pulse using the self-interference arrangement of FIG. 5.
Figure 10:
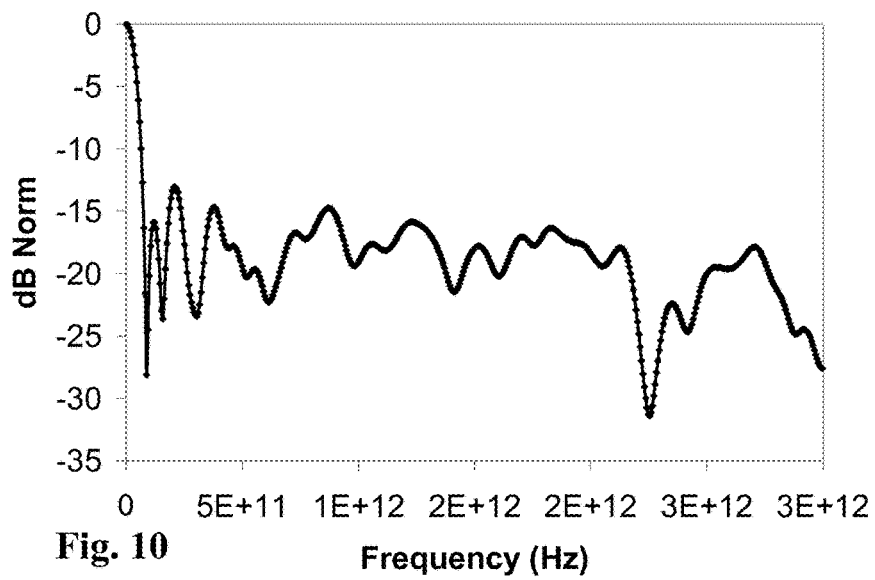
FIG. 10 shows the Fourier spectrum of the pulse shown in FIG. 9.
Figure 11:
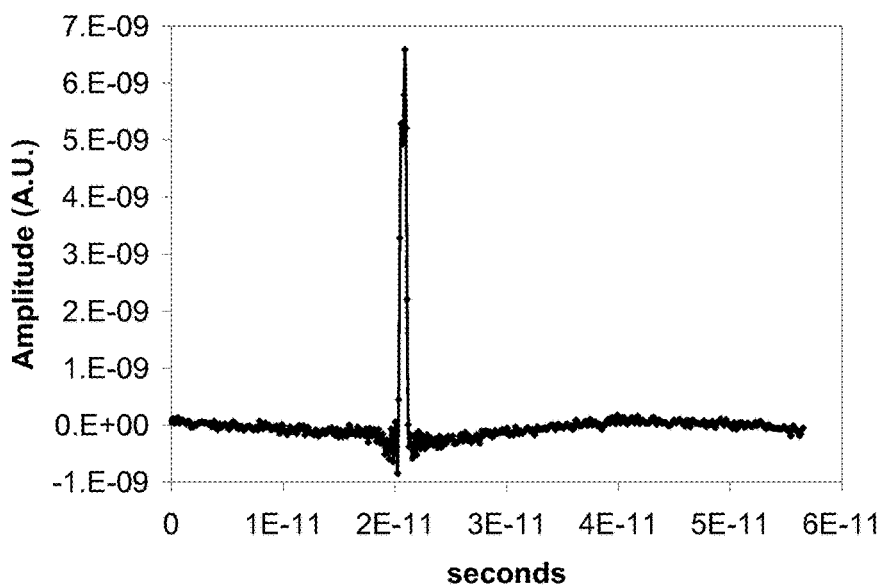
FIG. 11 shows a picosecond pulse using the embodiment of FIG. 4.
Figure 12:
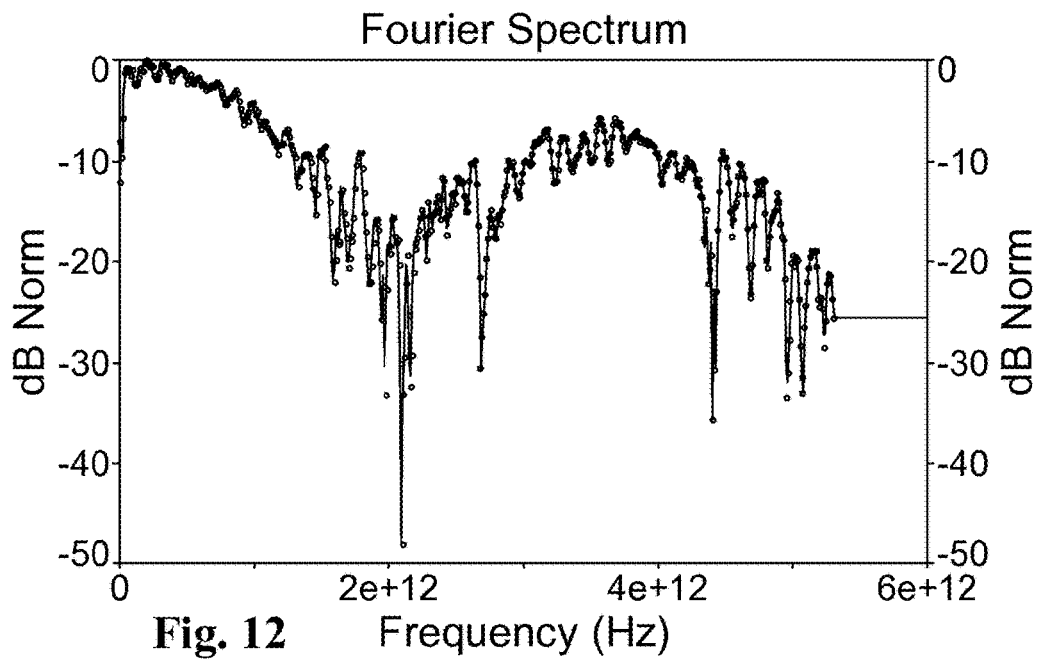
FIG. 12 shows the Fourier spectrum of the pulse shown in FIG. 11.

FIG. 9 shows a time-domain pulse obtained from the self-interference setup of FIG. 5 and FIG. 10 shows the corresponding frequency domain spectrum obtained via Fourier transform that spans up to 3 THz. FIG. 11 and FIG. 12 exhibit another example of pico-second pulse and terahertz spectrum from the configuration of FIG. 3. Here the THz range spans up to 5.5 THz.

All of the above spectra are taken without any specimen or specimen holder in the beam path.

A gap-free broadband terahertz spectrum is obtainable using dendrimer emitters. There are two main material advantages with dendrimer emitters that can explain the gap-free broadband THz spectrum from the THz emitter and sensor system. First, there is no lattice resonance region existing for our dendrimer films, so there is no phonon absorption in the THz regime, as there is no Reststrahlen band. Second, the phase mismatch in the dendrimer film is much smaller than EO crystals, so the first spectrum dip due to the phase mismatching is well above 10 THz; thus, there is no theoretical impediment to make a source with a frequency span ~10 THz or more. By reducing the thickness of the polymer film, this number can be pushed to a higher value. It is possible to engineer the refractive index of dendrimer materials to achieve almost perfect phase matching.

A terahertz time-domain spectrometer is discussed that utilizes the high efficient terahertz source and terahertz sampling sensor. The terahertz radiation (T-ray) generated by this source can be used for molecular signature recognition via terahertz time-domain spectroscopy (THz-TDS). Information available from THZ-TDS is usually not available from other methods such as FTIR. A better comprehension of biomolecular function and activity in vivo requires a detailed picture of biopolymer secondary and tertiary structures and their dynamical motions on a range of timescales. In order to directly monitor complex macromolecule dynamics in real time, an atomic level picture of the concerted motions of polypeptide chains and DNAs may be accessible through accurate measurement of low-frequency vibrational spectra. These vibrations are expected to occur in the terahertz (THz) frequency regime and may be observed using Raman, low-energy neutron and infrared absorption spectroscopes or related optical techniques. However, for even naturally occurring proteins and DNAs with >30 kDa molecular weights and large numbers of constituent peptide units or bases, one would expect the density of overlapping states to be so high in this frequency range that contributing absorption bands would smear out resulting in essentially structureless spectra. It would clearly be of priority to obtain low-frequency vibrationally resolved spectra for biological systems in aqueous-phase environments, because, this condition would most closely mimic their natural environment. However, this scenario has not been immediately feasible for most systems using far-infrared absorption spectroscopy because (a) absorption by the amino acids and most other biomolecules is masked by much stronger water absorption in the 1 to 3 THz spectral region and (b) spectral broadening arising from the full accessibility to conformational space and the rapid time scale for inter-conversion in these environments. Despite this limitation, recent terahertz absorption measurements of biomolecules in aqueous environments have revealed detailed information about the dynamics of these systems.

Spectral THz absorption data of DNA samples based on a dendrimer source and sensor and measured by the inventive THZ-TDS is discussed below. The initial results of THz-TDS measurements on DNA samples via dendrimer approach are also discussed below. The data exhibits the effectiveness of the THZ-TDS approach in discerning between the single-stranded DNAs (ssDNA) and double stranded DNAs (dsDNA), as well as quantitation of biologically available quantity (~pica mole) of biomaterials.

Two complementary 25-mer oligonucleotides were synthesized at the Macromolecular Synthesis Lab., having the sequences: TCT TCG CAC TAT CCC MG ATC TGA G (MW 7576.9 g) and CTC AGA TCT TGG GAT AGT GCG AAG A (MW 7746.1 g). The samples were applied onto 1 cm spots on microscope slides as both individual strands and hybridized duplex DNAs at different concentrations. The concentration of both single stranded DNA (ssDNA) and double stranded DNA (dsDNA) were varied over a range of nanomole to femtomole. The first 4 samples are marked "Yellow": Yellow-A and Yellow-B are each one of the two complementary ssDNA, each having 0.272 nMole of the ssDNA applied on the sample spot on the slide; Yellow-C and Yellow-D are dsDNA created by hybridizing equal amounts of each of the two complementary ssDNA strands to form the duplex (hybridized) DNA strands. Yellow-C has a total DNA amount of 0.272 nMole of Yellow-A and 0.272 nMole of Yellow-B in the spot (i.e., same MOLAR amount of dsDNA as in the ssDNA spots, but twice the total MASS of DNA as is in each ssDNA spot) and Yellow-D has 0.136 nMole of Yellow-A and 0.136 nMole of Yellow-B in the spot (i.e., half the MOLAR amount of dsDNA compared to the ssDNA spots, but the same total MASS of DNA as is in each ssDNA spot). The second four samples marked Orange had similar compositions but 100 times diluted; their respective weights were Orange-A, Orange-B, each 2.72 pMole, and Orange-C and Orange-D 1.36 pMole each. Two other groups, Green and White had 1000 times dilution and 10000 times dilution with respect to the Yellow samples.

The 25-mers described above are the same size as many existing microarrays, therefore, these samples would serve as a test to assessing the THZ-TD spectrometer's functionality and effectiveness to sensitively detect the hybridization of known DNA probes to create DNA-DNA complementary pairings with, for example, DNA from toxic organisms (possible biodefense usages, or field toxicology/environmental analyses), or to detect the differences between single-strand RNA (ssRNA) and ssDNA and their bound hybridized pairs, which might allow the technology to eliminate the need for expensive dyes and complex sample handling for the quantitation of messenger RNA (mRNA) abundances, as currently used, for example, to study the differences in gene expression between normal and diseased tissue, or normal and drug-treated cells.

In protein interaction studies, it is critical to determine the role of conformation state and protein flexibility. Changes of state, photobleaching, and photocycling often involve restrained changes in tertiary structure. Also, conformational change can often be decomposed into the collective vibrational modes that would constitute such a motion. Conformational vibrational modes are distinct from the familiar mid-infrared or infrared vibrational modes, which in general involve the motion of only pairs or small groups of molecules. Conformational modes involve the collective motion of entire subunits of the protein with 50-100 atoms moving in concert. These modes lay in the far infrared (FIR) with frequencies between 0.03 and 6 THz (1 and 200 cm$^{-1}$). One can then quantify conformational flexibility in terms of the density and spectrum of these low frequency collective vibrational modes.

Optical micrographs were taken of as received samples to inspect their texture and other observable features and are shown in FIGS. 14a-d. Some pictures showed dewetting and/or irregular wetting with presence of debris in some cases. Presence of bubbles and/or inclusions is also seen. In view of this morphological texture, it is surmised that the present work can be extended to incorporate additional DNA samples before a concrete conclusion is drawn.

Figure 15:
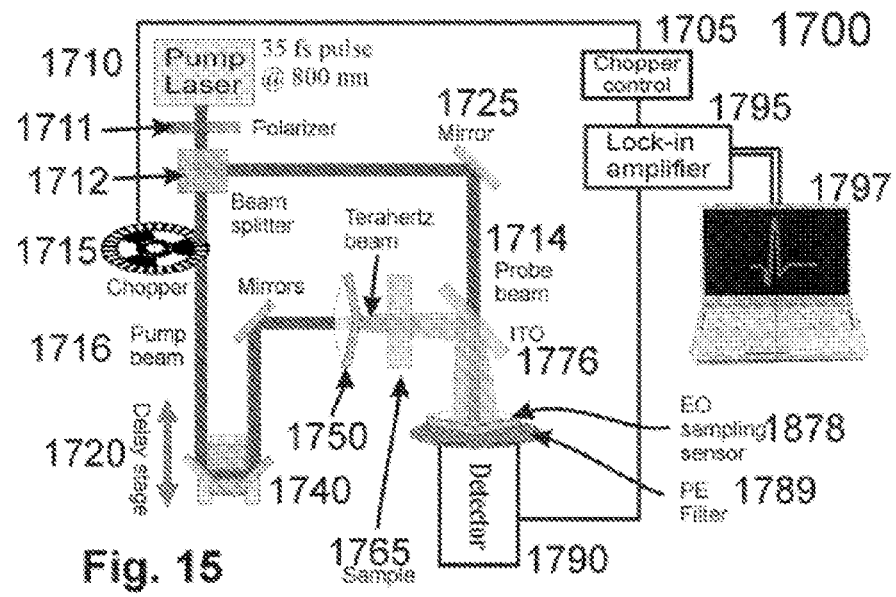
FIG. 15 shows another exemplary embodiment of a terahertz spectrometer.

Terahertz time-domain signals (aka, terahertz pulse, or temporal pulse) were collected from a terahertz spectrometer 1700 shown in FIG. 15 by an automated setup. In particular, terahertz spectrometer 1700 includes a pump laser 1710 such as for example, an 800 nm center wavelength femto-second pump laser. The beam from laser 1710 is split in to two parts by a beam splitter 1712 to establish a pump beam leg 1716 and a probe beam leg 1714. The pump beam in the pump beam leg 1716 is modulated by an optical chopper 1715 whose reference frequency is detected by a lock-in amplifier 1795. The lock-in amplifier 1795 reads in the detector 1790 responses at the reference frequency. The lock-in amplifier 1795 is controlled by a computer 1797 to read the transient (or temporal) pulse. The chopper control 1705 controls the frequency of the chopper within +/−0.5 Hz; this reference frequency is detected by the lock-in amplifier; the lock-in then measures the detector response at the detected reference frequency; thus, any noise present in the signal is eliminated up to the dynamic reserve of the lock-in (~30 dB).

The pump beam leg 1716 further includes a computer controlled delay stage 1720. The pump beam coming out of the delay stage 1720 is then reflected off mirrors 1740 and focused on terahertz emitter 1750, which is for example, a dendrimer film as processed above. Terahertz emitter 1750 produces a terahertz beam 1760 which is directed through a sample 1765 and reflected by an Indium Tin Oxide (ITO) block 1776. The probe beam leg 1714 is used as a probing beam that is reflected by a mirror 1725 and propagates through the ITO 1776. ITO 1776 is transparent to the probe beam in probe beam leg 1716 but reflects the terahertz beam; thus both beams are co-incident on the sampling sensor 1787 where pump beam can scan the stationary probe beam. From the electro-optic sensor 1787, the terahertz beam finally enters the detector 1790 through a 3.3 mm polyethylene filter that stops the pump beam from entering the detector; thus the detector measures the response due only to the terahertz beam, as described below.

Operationally, the glass slides containing the DNA samples are placed close to the terahertz emitter 1750 for a direct transmission under ambient conditions. T-rays were generated by focusing a 35 femto-second pulsed beam at 800 nm on a dendrimer emitter. The T-rays were transmitted through the specimen 1765 and then focused on a dendrimer sampling sensor 1787 that was probed by a femto-second pulsed beam. Both the pump and the probing beams were obtained from a single femto-second pulsed laser (giving ~250 mW power) by splitting the output at approximately 40:60 ratios. The 60-arm was used as pump while the 40-arm was used for probing. Finally, a 3.3 mm thick polyethylene filter was used to cover the detector so that only the T-rays can contribute to the measured spectra.

First a temporal pulse of a blank substrate was acquired that serves as the background. Then the operation was repeated on Orange_A (ssDNA) and Orange_C (dsDNA) samples.

Figure 16:
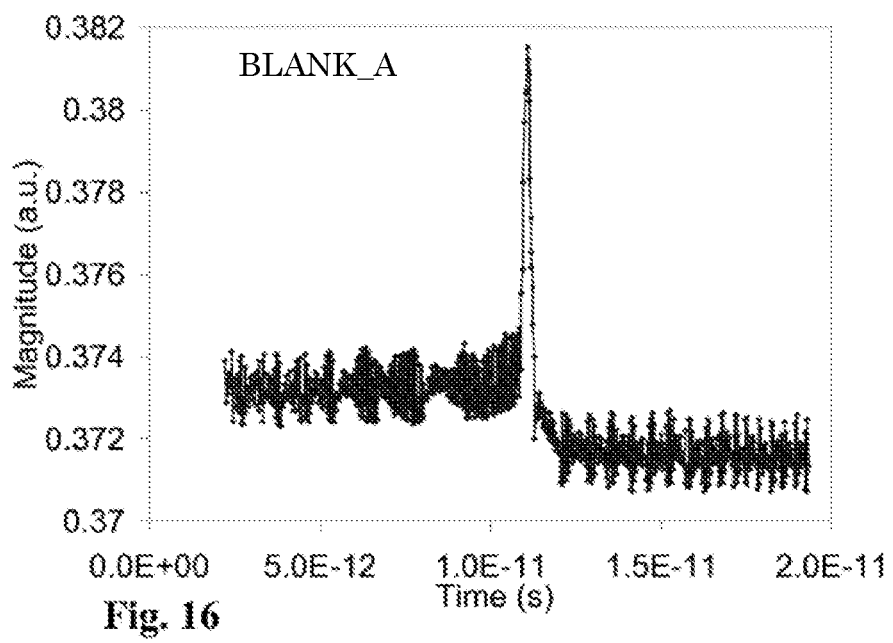
FIG. 16 shows a time domain temporal pulse of a blank substrate.
Figure 17:
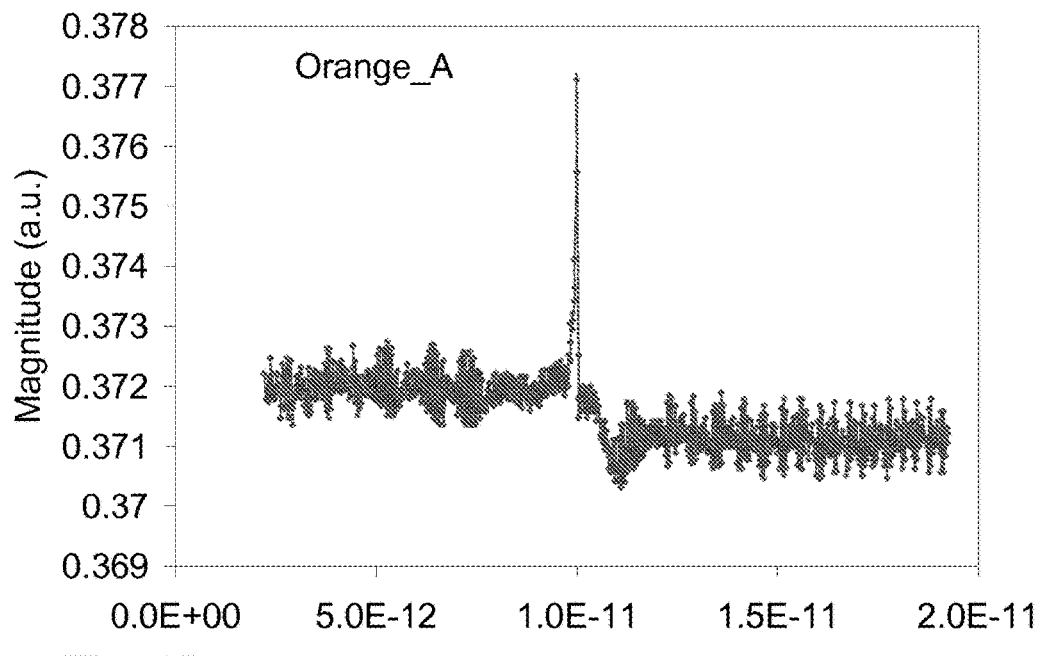
FIG. 17 shows a time domain temporal pulse of a ssDNA sample from Orange group.
Figure 18:
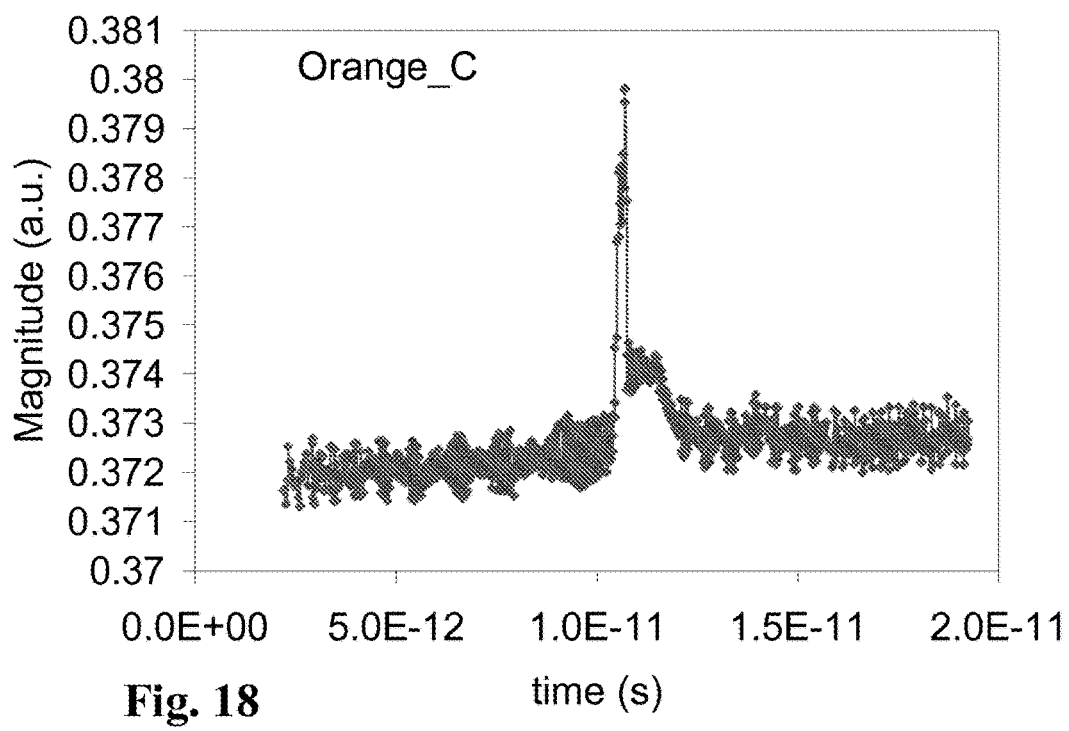
FIG. 18 shows a time domain temporal pulse of a dsDNA sample from Orange group.
Figure 19A:
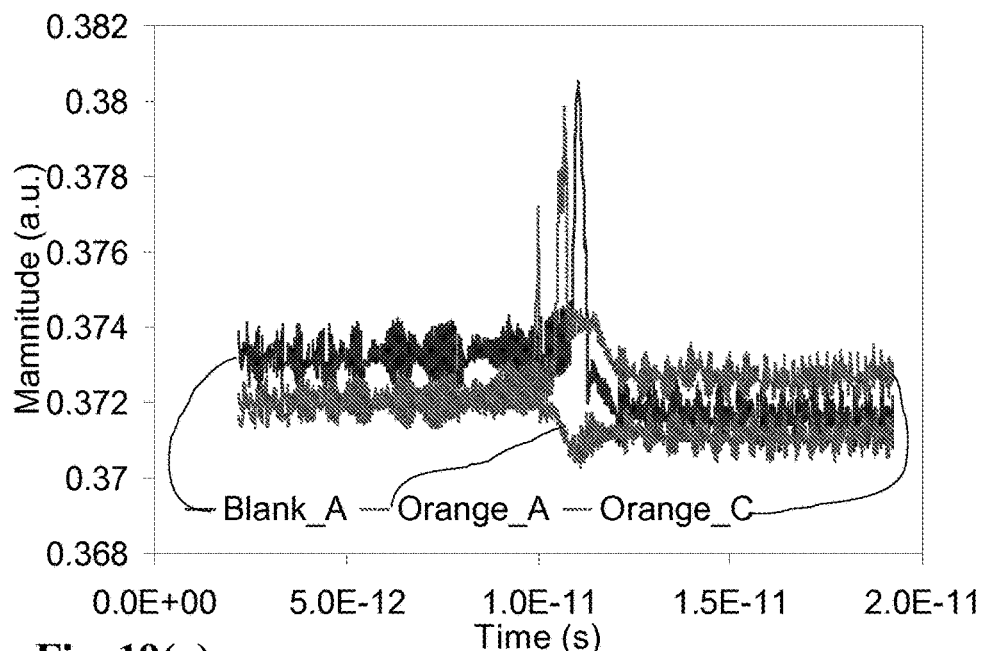
FIG. 19A shows a multiplot of time domain temporal pulses of blank substrate, ssDNA and dsDNA samples from Orange group.
Figure 19B:
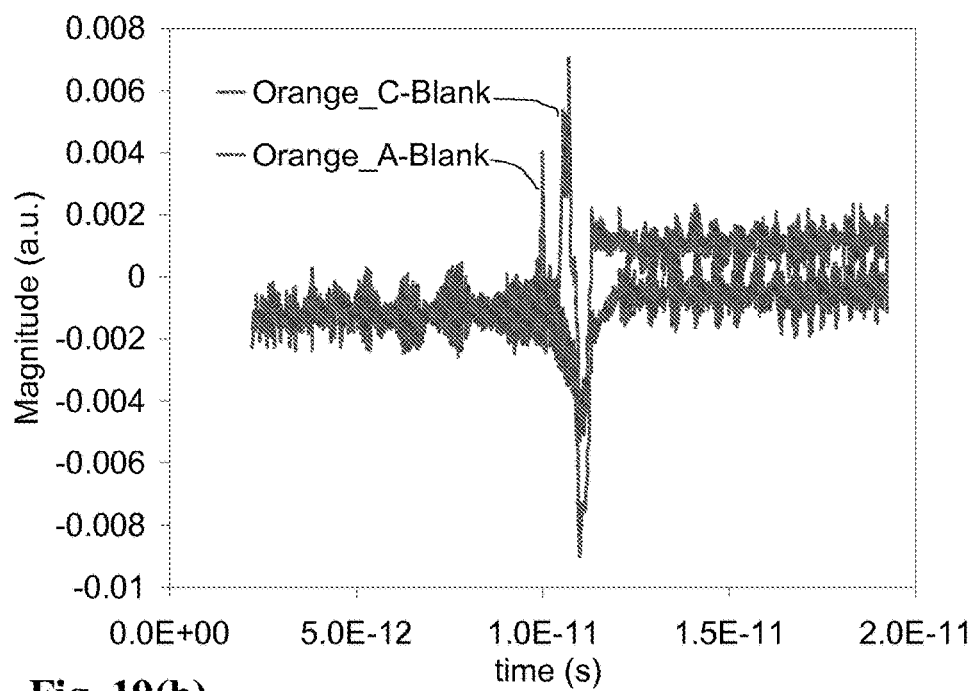
FIG. 19B shows a multiplot of time domain temporal pulses of ssDNA and dsDNA samples from Orange group obtained by subtracting from blank substrate pulse.

FIGS. 16-18 exhibit the temporal time-domain spectra of a Blank, Orange_A (ssDNA) and Orange_C (dsDNA) samples. FIG. 19A shows a combined plot of these temporal spectra. FIG. 19B shows the temporal time-domain spectra of Orange_A (ssDNA) and Orange_C (dsDNA) samples obtained by subtracting the background (Blank substrate), thus revealing the temporal behavior of the ssDNA and the dsDNA.

Figure 20:
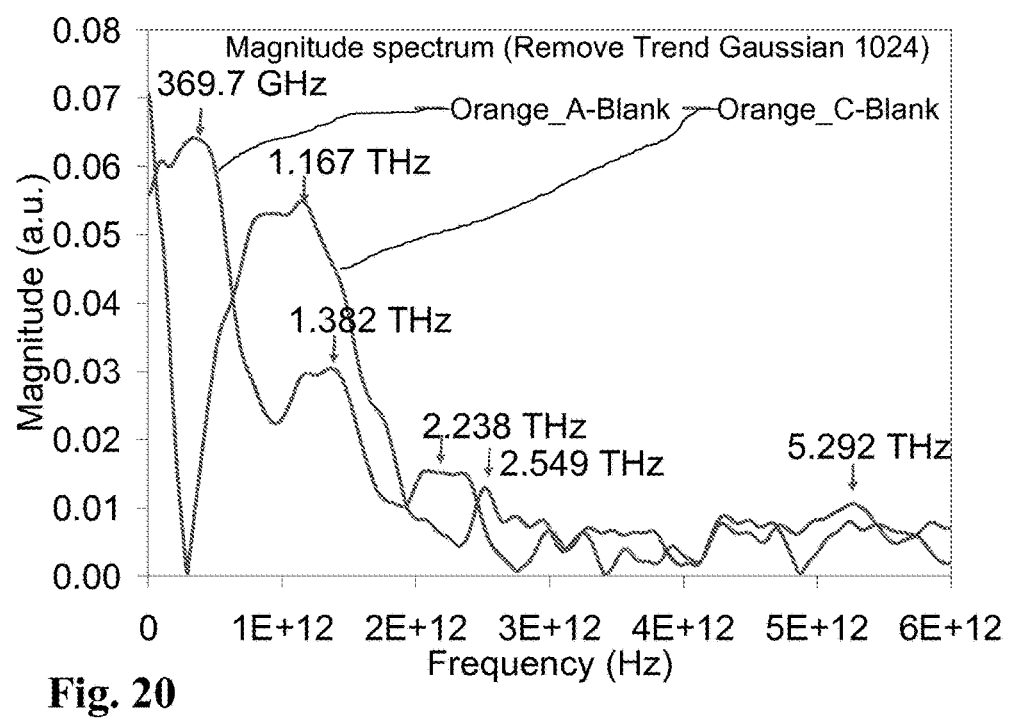
FIG. 20 shows the magnitude spectra of the ssDNA and dsDNA from Orange group for pulses shown in FIG. 19B.

FIG. 20 shows the magnitude spectra of the ssDNA and dsDNA samples. These spectra were obtained by fast Fourier analysis of the temporal time-domain spectra shown in FIG. 19B. For each species, three different peaks can be identified for both ssDNA and dsDNA; however, the peaks are significantly shifted compared to each other, thus allowing an easy comparison and a means of identifying the respective species.

Figure 21:
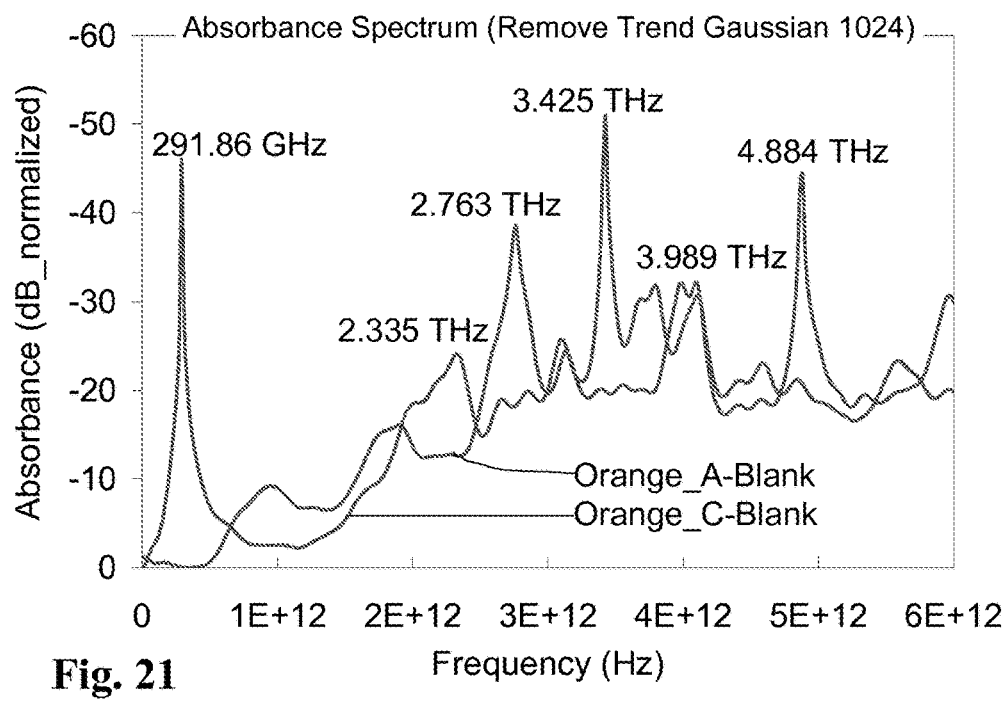
FIG. 21 shows the absorbance spectra of the ssDNA and dsDNA from Orange group for pulses shown in FIG. 19B.

FIG. 21 shows the absorbance spectra of the same samples, also obtained by fast Fourier analysis of the temporal time-domain spectra. These spectra reveal the presence of sharp absorbance peaks that are shifted significantly with respect to each other. While the location of these peaks will be confirmed by additional measurements, however, a clear distinction is visible between the spectra of the ssDNA and the dsDNA samples, thus allowing a means of comparing and identifying the respective species.

Figure 22:
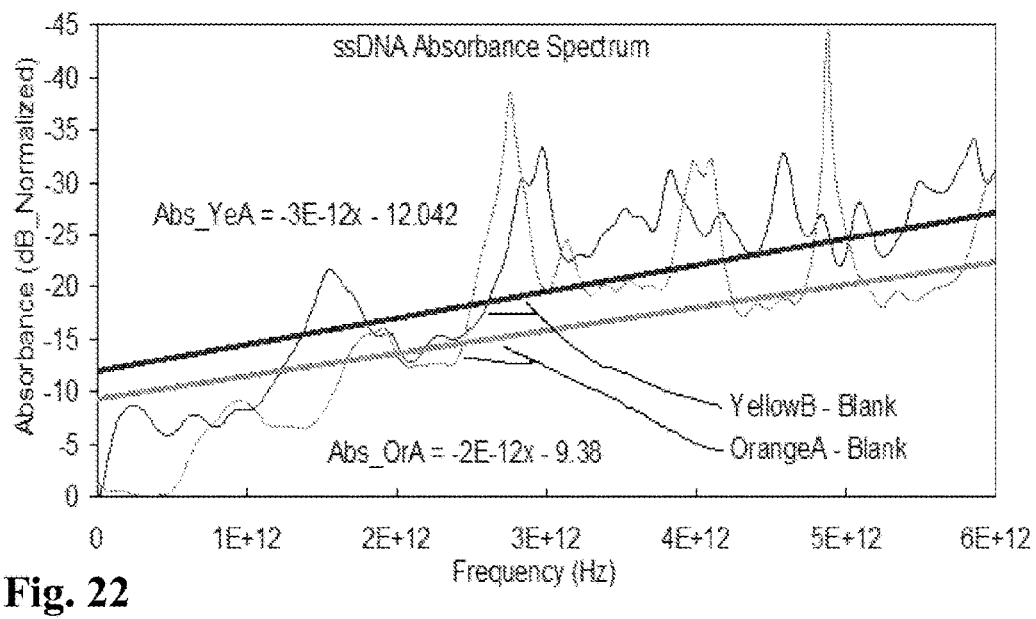
FIG. 22 shows the absorbance spectra of sDNA of two different concentrations.

The unique properties of terahertz spectroscopy make it a powerful technique to detect and quantify signals from biologically available amounts of material. FIG. 22 shows absorbance spectra of the 25 mer ssDNA nucleotide samples of the present investigation. The YellowB sample has a higher molar concentration (0.272 nMole) than the OrangeA (2.72 pMole). As such the YellowB sample has a higher absorption than OrangeA. The slope and the intercept of the line fitted through the absorbance curves are higher for higher concentration. This gives a clear indication that the THz-TDS technique can be used for quantitation of very small amount of DNA.

From the results presented, it is demonstrated that the THz-TDS and the spectrometer offer an effective technique to discern between the complementary 25-mer oligonucleotides. The spectral range of the instrument is enough to resolve spectral characteristics up to 6 THz. This range was limited by the femto-laser that was used for this disclosure; however, the range can be extended by utilizing different laser combinations. The sensitivity of the instrument is also good enough to discern between the single stranded and double stranded DNA of identical mass as well as for quantitation of DNAs of different but small amount of mass, ~pico-moles to femto-moles.

Figure 23:
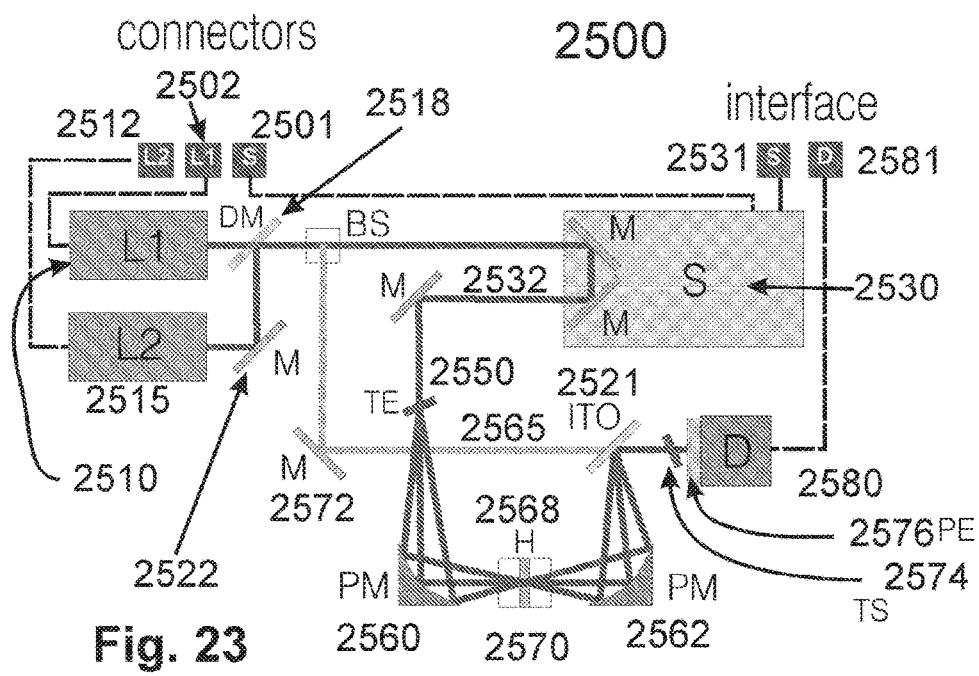
FIG. 23 shows another exemplary embodiment of a terahertz spectrometer utilizing difference frequency mixing and a stationary sample arrangement.

Referring now to FIG. 23, there is terahertz DFG (aka DFM) spectrometer 2500 which includes a pump laser 2510 such as for example, a 980 nm center wavelength continuous wave (CW) diode laser that is powered by a connector 2502. Provided also another CW diode laser 2515 such as for example, one with 1064 nm center wavelength that is powered by the connector 2512. The beams emerging from both lasers are combined by means of mirror 2522 and a Dichroic mirror 2518 and then split in to two parts by a beam splitter 2522 to establish a pump beam leg 2528 and a probe beam leg 2565. The pump beam in the pump beam leg 2528 may be modulated by an optical chopper for pyroelectric detection. For CW diode laser pumps, a chopper is not necessary. A thermopile type detector interfaced with a PC via port 2581 is used in the later case to detect the terahertz radiation.

The pump beam leg 2528 further includes a computer controlled delay stage 2530 that is powered via connector 2501 and interfaced with a computer via port 2531. The pump beam coming out of the delay stage 2530 is then reflected off mirrors 2535 and focused on terahertz emitter 2550, which is for example, a dendrimer film as processed above. Terahertz emitter 2550 produces a diverging terahertz beam 2568 which is reflected off of a parabolic mirror 2560 and then focused on a sample 2570 by the parabolic mirror 2560. The terahertz beam is then reflected off of a second parabolic mirror 2562 which focuses the beam on the Indium Tin Oxide (ITO) block 2521. The probe beam leg 2565 is used as a probing beam that is reflected by a mirror 2572 and through the ITO 2521 incidents on the electro-optic terahertz sensor 2574. ITO block 2521 is transparent to the probe beam in probe beam leg 2565. The pump beam is reflected off of the ITO 2521 and co-incident onto the electro-optic terahertz sensor 2574. From there the resultant beam proceeds to the detector through a 3.3 mm polyethylene filter that stops any pump or probe beams from entering the detector. Thus the detector measures only the response due to terahertz radiation.

Operationally, the glass slides containing the DNA samples are placed on the sample holder H located at the focal point of the parabolic mirror 2560. T-rays were generated by the difference frequency mixing of the beams from both diode lasers 2510 and 2515. The T-rays were transmitted through the specimen 2570 and then focused on a dendrimer sampling sensor 2574 that was probed by a probing beam 2565. Both the pump and the probing beams were obtained from a single pair of diode lasers (giving ~800 mW combined power) by splitting the output at approximately 30:70 ratio. The 70-arm was used as pump while the 30-arm was used for probing. Finally, a 3.3 mm thick polyethylene filter was used to cover the detector so that only the T-rays can contribute to the measured spectra.

Figure 24:
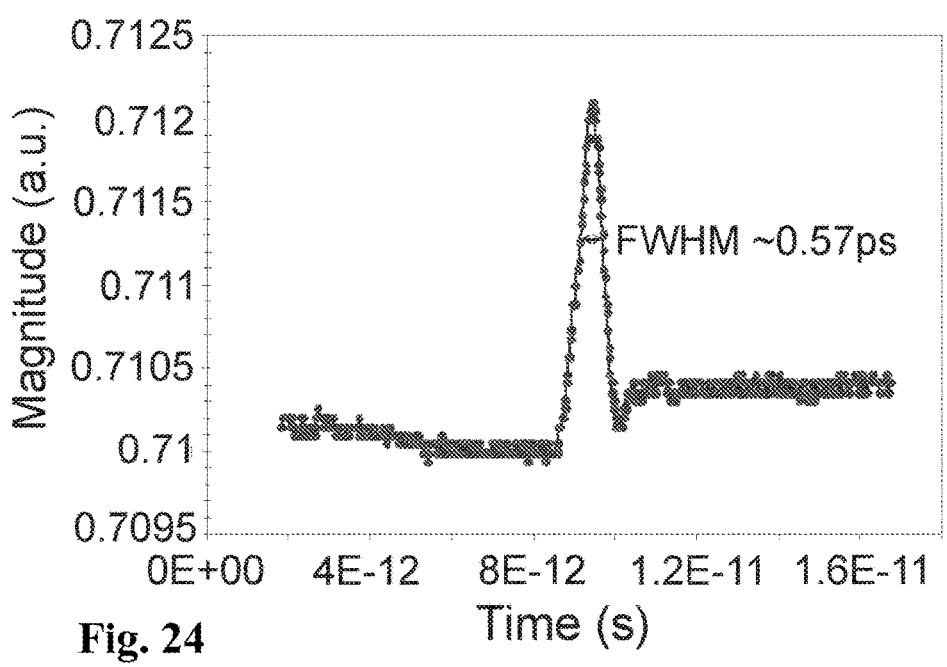
FIG. 24 exhibits an exemplary temporal pulse obtained from the setup of FIG. 23.
Figure 25:
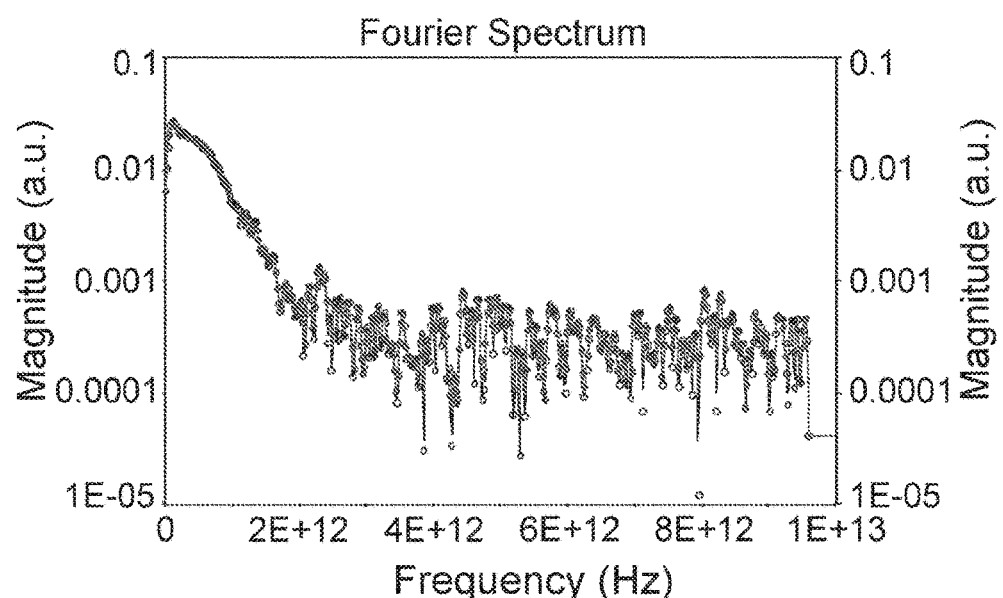
FIG. 25 shows a Fourier transform spectrum of the pulse of FIG. 24.

Terahertz time-domain signals (aka, terahertz pulse, or temporal pulse) were collected from the DFG terahertz spectrometer 2500 shown in FIG. 23 by an automated setup via above mentioned procedure. FIG. 24 shows a temporal pulse acquired from the DFG spectrometer setup. Here the X-axis is measured as the actual motion of the delay stage. Assuming there is no change in the refractive index, a time domain plot can be generated, as shown in FIG. 24. FIG. 25 shows a Fourier transform magnitude spectrum of the temporal signal shown in FIG. 24. The frequency spans over ~10 THz, however, the noise is higher in the higher frequency region. This frequency range is useful for investigating biological molecules.

Figure 26:
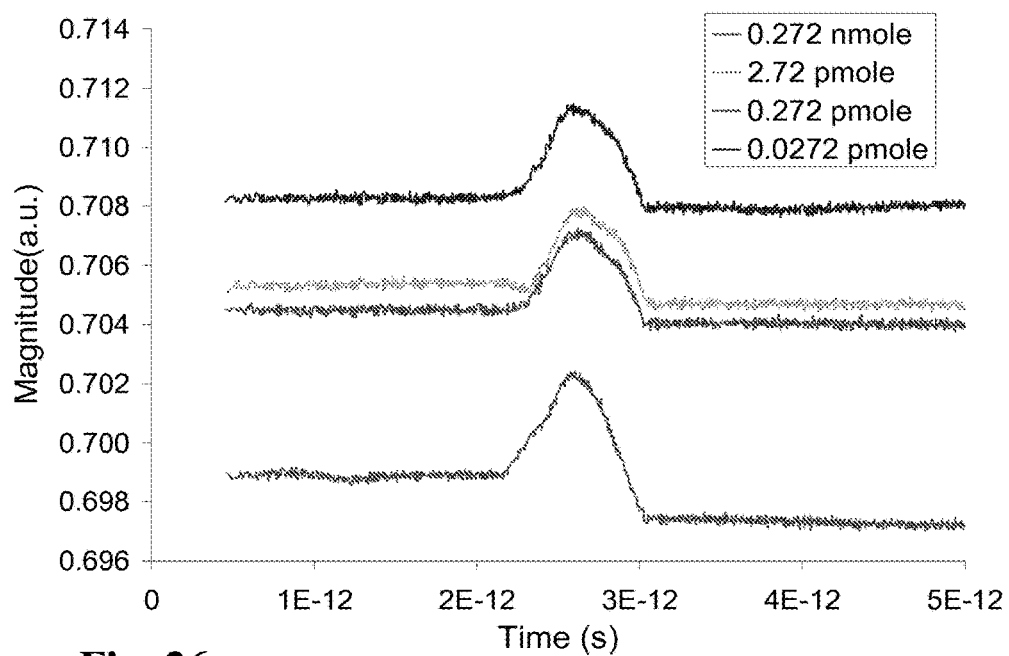
FIG. 26 shows a series of pulse obtained from dsDNA samples.
Figure 27:
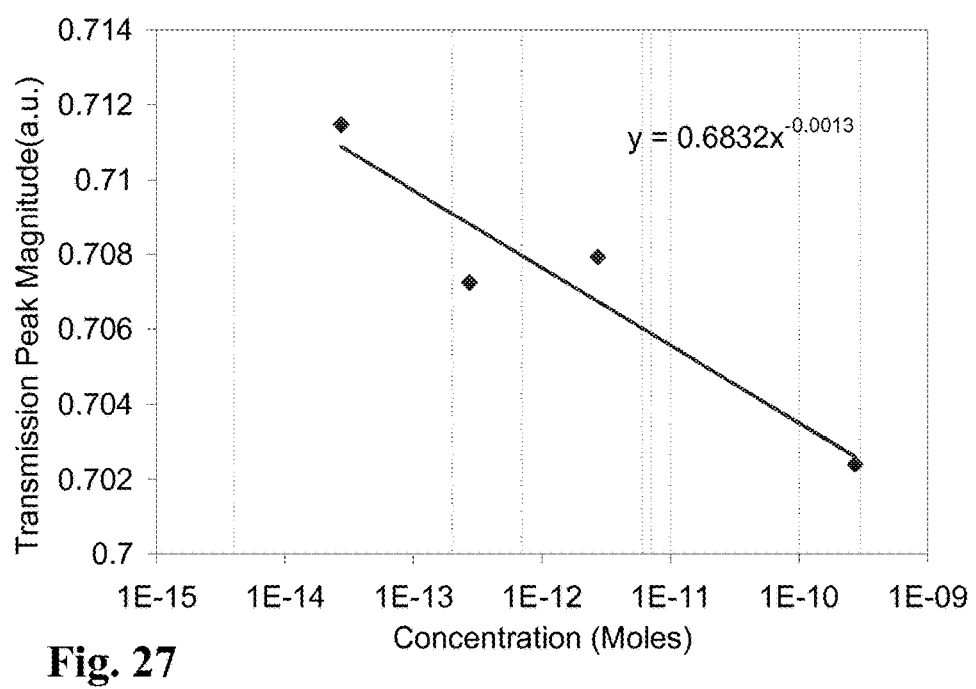
FIG. 27 shows the dose dependence of dsDNA samples.

FIG. 26 exhibits a series of temporal transmission spectra corresponding to specimens of different concentration (dose). These spectra were collected at normal temperature and atmosphere. The peak transmission extracted from the temporal spectra of the double stranded DNA samples exhibit a power law behavior over a region spanning from 27.2 femto-moles to 0.272 nano-moles (see FIG. 27). The results clearly demonstrate the ability of the spectrometer to discern a minute amount of biomolecules in a label-free fashion. From measurements of known concentration, calibration curves can be established for different molecular species. The importance of this ability is in the fact that it will be able to identify a disease causing pathogen that may bind to the DNA and eventually resulting in DNA mutation. This capability can be used as a diagnostic tool, as well as for studying molecular reactions such as mutation or polymorphism. Further, Fourier transform of these temporal pulses will reveal the frequency domain signature of a given species. Therefore, a combined knowledge from the temporal pulse and the frequency domain spectrum will establish a unique capability of molecular identification and detection.

Figure 28:
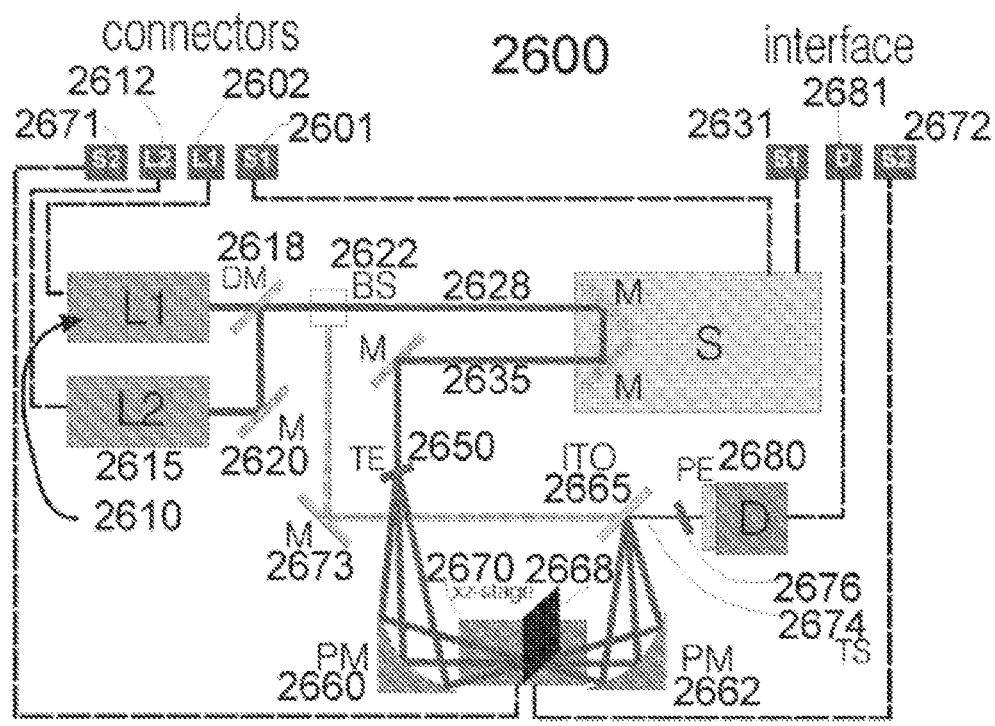
FIG. 28 shows an exemplary embodiment of a scanning terahertz spectrometer utilizing difference frequency mixing.

Referring now to FIG. 28, there is provided a terahertz scanning spectrometer 2600. Terahertz spectrometer 2600 includes dual pump lasers 2610 and 2615 powered through power connectors 2602 and 2612, respectively. Both lasers 2610 and 2615 are either diode lasers (DL) or diode pumped solid state (DPSS) lasers of appropriate but different wavelength. A first pump beam from laser 2610 passes through a Dichroic mirror 2618 and a second pump beam from laser 2615 reflects off of mirror 2620 towards the dichroic mirror 2618. The combined pump beam is then split in to two parts by a beam splitter 2622 to establish a pump beam leg 2628 and a probe beam leg 2626. The pump beam leg 2628 further includes a computer controlled delay stage 2630 powered through power connector 2601 and computer controlled via interface 2631. The pump beam coming out of the delay stage 2630 is then reflected off mirrors 2635 and focused on terahertz emitter 2650, which is for example, a dendrimer film as processed above. Terahertz emitter 2650 produces a terahertz beam which is focused onto the parabolic mirror 2660 and then focused on to a sample 2668 placed on a scanning sample holder 2670; a second parabolic mirror 2662 reflects the beam on to an ITO terahertz reflector 2665 which then steers the beam on to a electro-optic terahertz sensor 2674. The probe beam leg 2626 is used as a probing beam that is reflected by a mirror 2672 and through the ITO terahertz reflector 2665. The pump beam and probe beam both impact the terahertz sensor 2674. A polyethylene filter 2676 covers a detector 2680 so that only the T-rays can contribute to the measured spectra. Detector 2680 is interfaced to a computer control via interface 2681.

The xz stage 2670 provides an ability to scan plurality of sample spots on a single substrate. The scanning resolution may be ~0.098 pm in any lateral direction. With modern lithography printing technique, sample spots may be as small as a few microns diameter.

Figure 29:
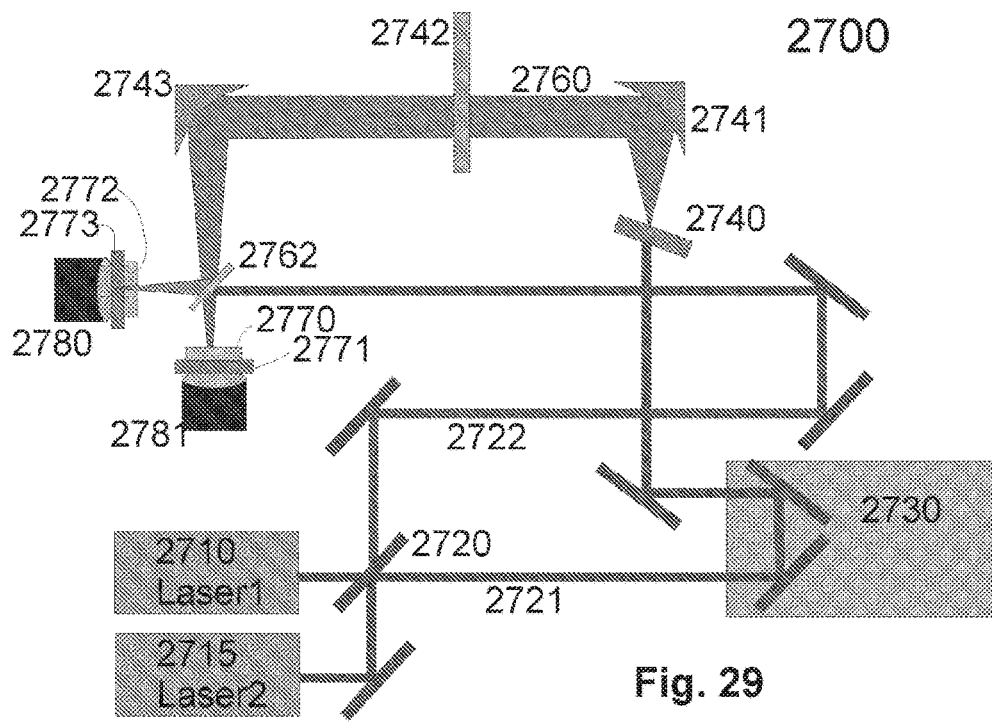
FIG. 29 shows an exemplary embodiment of a terahertz spectrometer utilizing two different detectors.

FIG. 29 exhibits yet another embodiment of the DFG spectrometer 2700 that involves two detectors 2760 and 2781. Other relevant parts of DFG spectrometer as in FIG. 23 is incorporated in FIG. 29 by reference. The two detectors are useful in measuring both the real and imaginary components of the terahertz signal that enables to extract both real and imaginary parts of an observable such as the refractive index. The operational principle of the spectrometer in FIG. 29 is the same as that described for the spectrometer shown in FIG. 23. That is the pump beams from laser 2710 and 2715 are combined and then split with a beam splitter 2720 in to a pump beam and a probing beam 2722. The pump beam is incident on the dendrimer terahertz emitter 2740 and the emitted terahertz beam is focused on the parabolic mirror such that the 90° reflected terahertz beam 2760 is collimated. A sample is located on a xyz stage 2742 that is exposed to the collimated terahertz beam 2760. After transmission through the specimen, the beam 2760 is reflected off of a second parabolic mirror 2743 that focuses the terahertz beam on a beam splitter 2762. The resulting two arms of the beam is directed to the detectors 2780 and 2781 that passes through electro-optic terahertz sensors 2772 and 2770 respectively. Prior to entering the detectors the beams also pass through polyethylene filters 2773 and 2771 so that the detector measures the response due to terahertz radiation alone.

Figure 30:
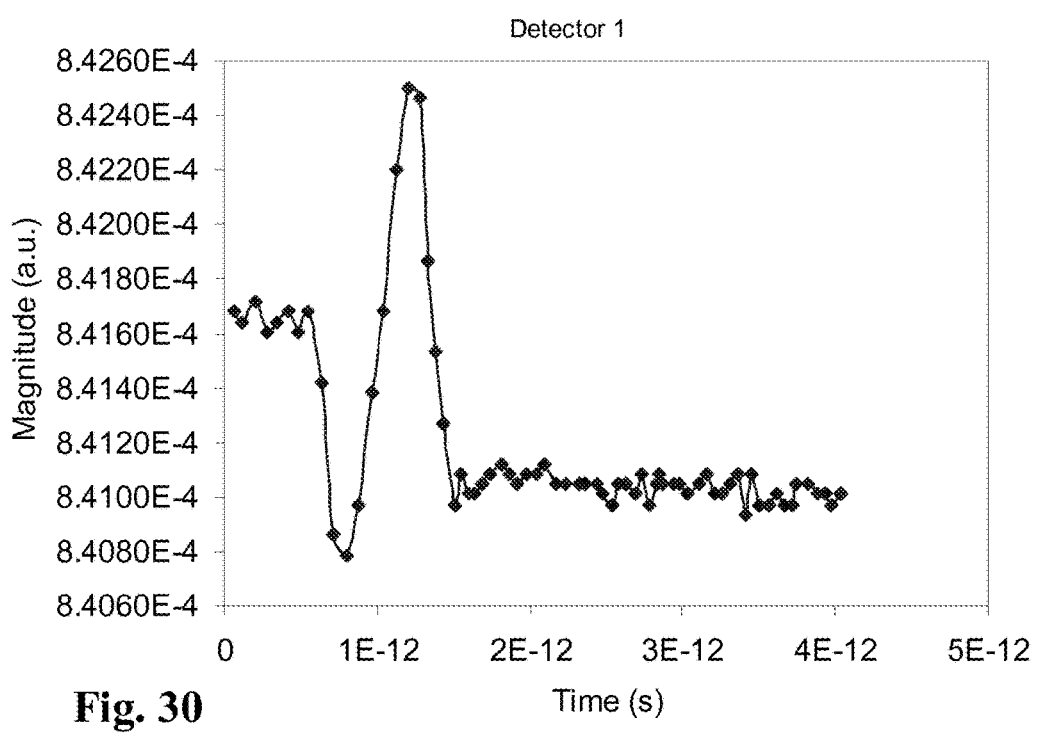
FIG. 30 shows an exemplary response for the embodiment shown in FIG. 29.
Figure 31:
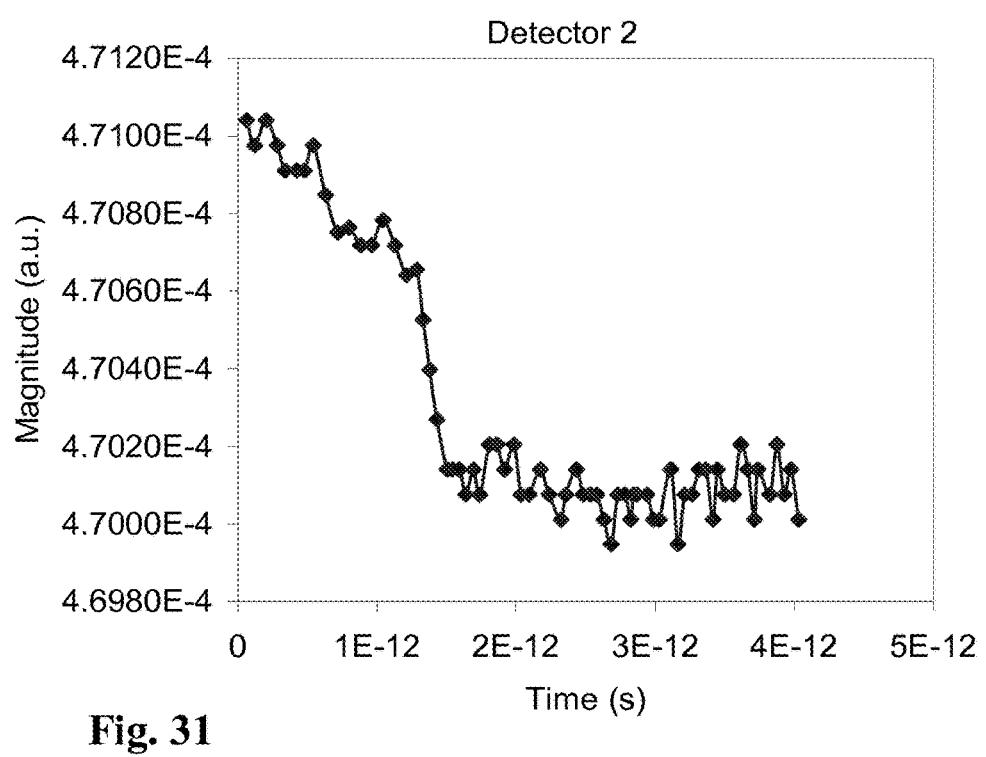
FIG. 31 shows an exemplary response for the embodiment shown in FIG. 29.
Figure 32:
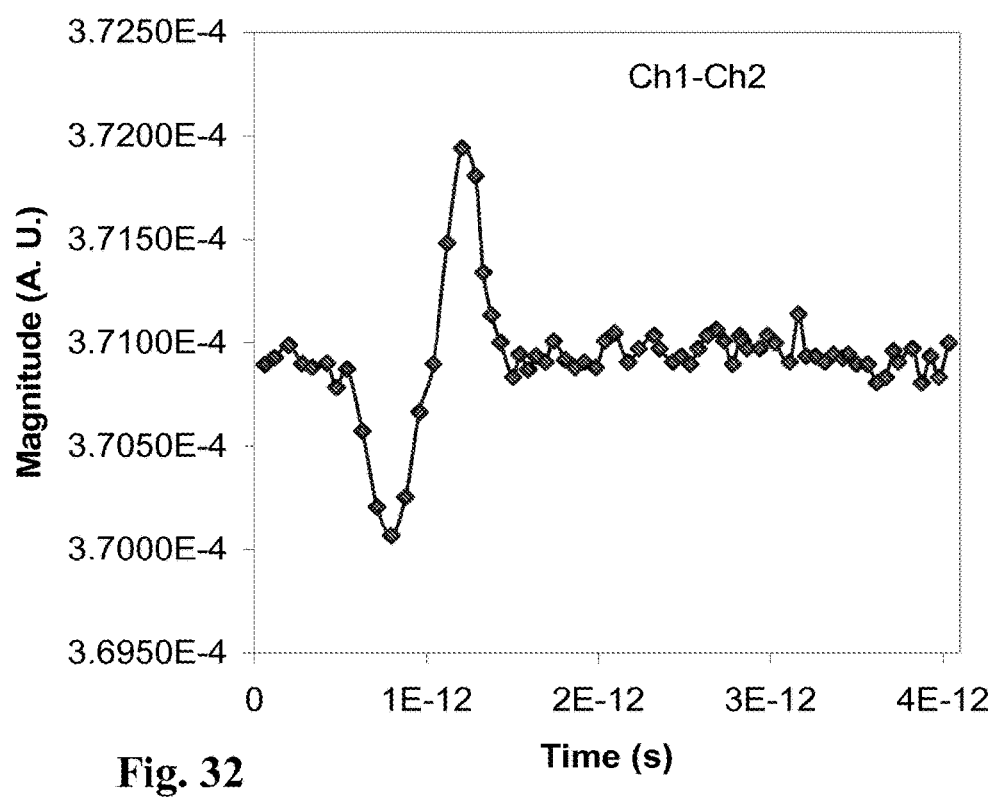
FIG. 32 shows an exemplary response for the embodiment shown in FIG. 29.
Figure 33:
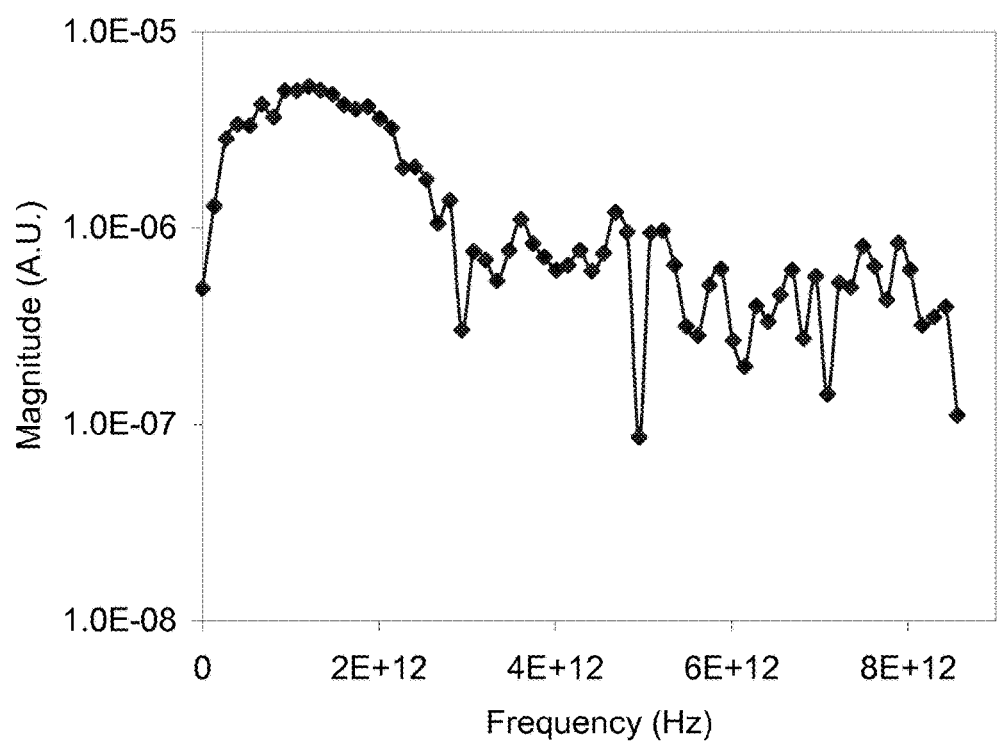
FIG. 33 shows an exemplary response for the embodiment shown in FIG. 29.

FIG. 30-31 shows the response obtained from both detectors of the spectrometer in FIG. 29. The difference frequency response is obtained by taking the difference of both detectors, as shown in FIG. 32. A fast Fourier transform frequency spectrum of FIG. 32 is shown in FIG. 33. The frequency for this setup spans up to 8.5 THz with the prominent peak lying between 1.5 THz and 2.0 THz.

Figure 34:
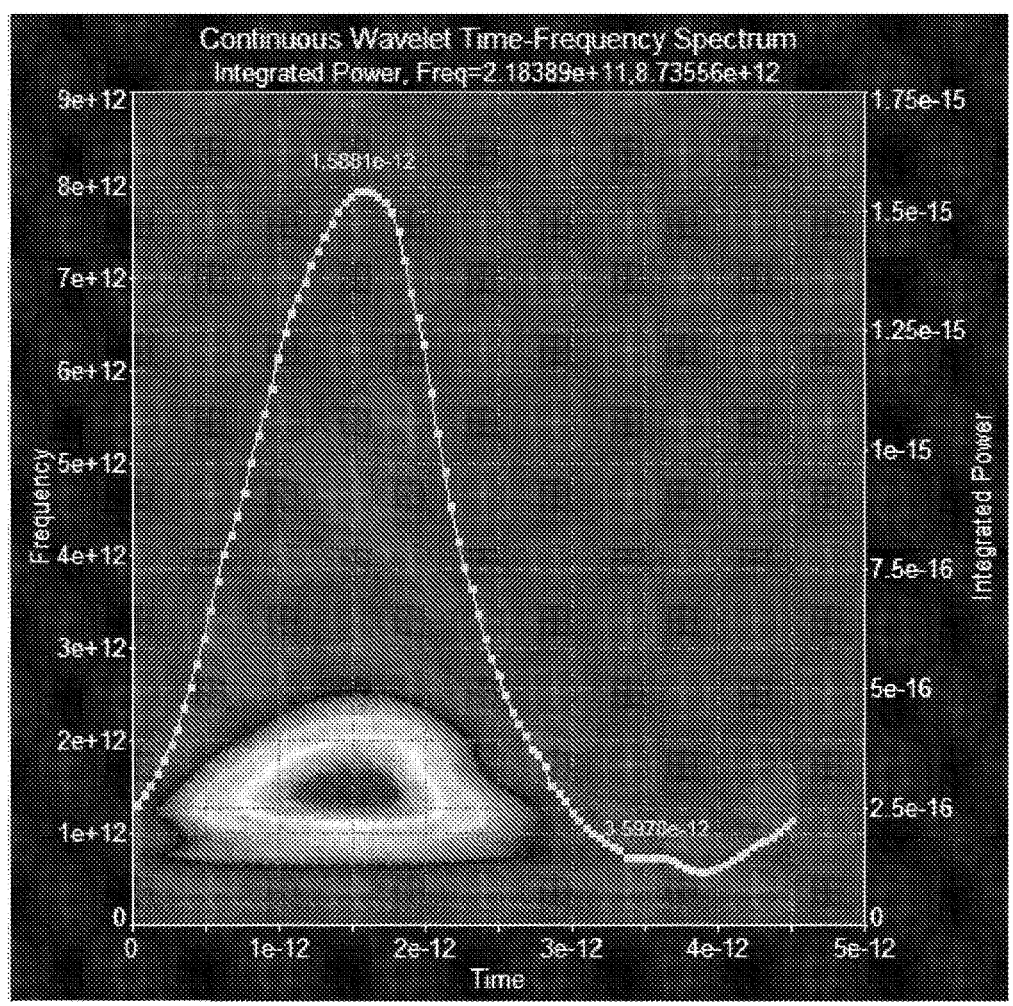
FIG. 34 shows a wavelet transform diagram of the data shown in FIG. 32.

FIG. 34 shows a wavelet transform diagram of the data shown in FIG. 32. The Fourier transform takes a signal in the time domain and transforms it into the frequency domain, where the Fourier transform result represents the frequency components of the signal. However, once the signal is transformed into the frequency domain, we lose all information about time, only frequency remains. The wavelet transform gives the frequency domain information but it does preserve the time domain information as well. Often times a particular spectral component occurring at any instant can be of particular interest. In these cases it may be very beneficial to know the time intervals where these particular spectral components occur. Wavelet transform is capable of providing the time and frequency information simultaneously, hence giving a time-frequency representation of the signal, as can be seen from FIG. 34. Here the frequency maximum of ~8 THz occurs at a time 1.588 pico seconds.

A scanning specimen holder is provided wherein the specimen holder can scan a substrate containing plurality of specimen spots, wherein the spot size may be on the order of micron, wherein the specimen may be of biological or other molecular origin, wherein the specimen dose may vary from a few femto moles to a few moles.

Other embodiments of the invention will be apparent to those skilled in the art from a consideration of this specification or practice of the invention disclosed herein; the scope and spirit of the invention being indicated by the following claims.

The invention claimed is:

1. A spectrometer for analyzing a sample, comprising:
   a pair of lasers configured to generate a beam using difference frequency generation;
   a beam splitter configured to generate a pump beam and a probe beam from the beam;
   a first optical arrangement configured to focus a pump beam at a terahertz emitter; the terahertz emitter having a dendrimer film, positioned orthogonally with respect to the pump beam and in the path of the pump beam, wherein the terahertz emitter is configured to generate a diverging terahertz beam in the frequency range of 0-20 THz based on the pump beam, the diverging terahertz beam being reflected off a first mirror and focused on the sample,
   a second mirror configured to direct the diverging terahertz beam that has passed through the sample to a terahertz sensor;
   a second optical arrangement configured to focus the probe beam at the terahertz sensor; and
   a detector configured to detect a sample terahertz spectra from an interaction between the probe beam and the divergent terahertz beam.

2. The spectrometer of claim 1 wherein the first mirror is a first parabolic mirror and the second mirror is a second parabolic mirror.

3. The spectrometer of claim 1 wherein the first optical arrangement is a first mirror arrangements and the second optical arrangement is a second mirror arrangement.

4. The spectrometer of claim 1, wherein the terahertz emitter is poled at an elevated temperature by a high strength electric field to convert the dendrimer film to a uniaxial polar material.

5. The spectrometer of claim 1, wherein at least one picosecond temporal pulse is generated from interference between a pump beam and a probe beam, both being incident at the terahertz sensor.

6. The spectrometer of claim 5, further comprising a computer controlled detector to measure the temporal pulse.

7. The spectrometer of claim 1, wherein at least one picosecond temporal pulse is generated by the pump beam incident at the terahertz emitter in a self-interference configuration.

8. The spectrometer of claim 7, further comprising a computer controlled detector to measure the temporal pulse.

9. The spectrometer of claim 1, wherein the pump beam is modulated by a chopper at predetermined frequencies.

10. The spectrometer of claim 1, further comprising;
    a computer controlled lock-in amplifier;
    wherein the detector is a pyroelectric detector for detecting a peak voltage of beam interference; and
    the computer controlled lock-in amplifier reads the peak voltage of the pyroelectric detector at a modulating frequency.

11. The spectrometer of claim 1, wherein the detector detects at least one of reflected and transmitted radiation that contains information related to a specimen.

12. The spectrometer of claim 1, wherein the terahertz emitter's dipole orientation is aligned and frozen-in time.

13. The spectrometer of claim 1, further comprising:
    a specimen holder configured to hold at least one specimen, wherein the specimen holder is subject to the terahertz radiation and the detector is configured to detect one of a transmitted radiation or a reflected radiation from the at least one specimen.

14. The spectrometer of claim 13, further comprising:

a second detector;

wherein the detector is configured to detect a real component of one of a transmitted radiation or a reflected radiation from at least one specimen and the second detector is configured to detect an imaginary component of one of the transmitted or reflected radiation from the at least one specimen, and wherein the detections from the detector and the second detector are independent.

15. The spectrometer of claim 1, further comprising a scanning sample holder.

16. The spectrometer of claim 1, further comprising:

a second detector;

wherein the detector is configured to detect a real component of one of a transmitted radiation or a reflected radiation from at least one specimen and the second detector is configured to detect an imaginary component of one of the transmitted or reflected radiation from the at least one specimen, wherein detections from the detector and the second detector are independent.

* * * * *